US010401363B2

(12) United States Patent
Silva González et al.

(10) Patent No.: US 10,401,363 B2
(45) Date of Patent: Sep. 3, 2019

(54) MONOCLONAL ANTIBODY FOR THE DIAGNOSIS, TREATMENT AND/OR PREVENTION OF BRAIN TUMORS AND BRAIN LESIONS

(71) Applicants: ALTHIA HEALTH, S.L, Madrid (ES); CONSEJO SUPERIOR DE INVESTIGACIONES CIENTIFICAS (CSIC), Madrid (ES)

(72) Inventors: Augusto Silva González, Madrid (ES); José Alberto García Sanz, Madrid (ES)

(73) Assignees: ALTHIA HEALTH, S.L., Madrid (ES); CONSEJO SUPERIOR DE INVESTIGACIONES CIENTIFICAS, Madrid (ES)

(*) Notice: Subject to any disclaimer, the term of this patent is extended or adjusted under 35 U.S.C. 154(b) by 0 days.

(21) Appl. No.: 15/541,846

(22) PCT Filed: Dec. 17, 2015

(86) PCT No.: PCT/EP2015/080349
§ 371 (c)(1),
(2) Date: Jul. 6, 2017

(87) PCT Pub. No.: WO2016/097213
PCT Pub. Date: Jun. 23, 2016

(65) Prior Publication Data
US 2018/0011095 A1 Jan. 11, 2018

(30) Foreign Application Priority Data
Dec. 19, 2014 (EP) .................................... 14382545

(51) Int. Cl.
*G01N 33/574* (2006.01)
*A61K 49/18* (2006.01)
*C07K 16/18* (2006.01)
*C07K 16/28* (2006.01)
*C07K 16/30* (2006.01)
*G01N 33/543* (2006.01)
*A61K 39/00* (2006.01)

(52) U.S. Cl.
CPC ....... *G01N 33/574* (2013.01); *A61K 49/1875* (2013.01); *C07K 16/18* (2013.01); *C07K 16/2863* (2013.01); *C07K 16/3053* (2013.01); *G01N 33/54326* (2013.01); *G01N 33/57492* (2013.01); *A61K 2039/505* (2013.01); *G01N 2446/20* (2013.01); *G01N 2446/84* (2013.01)

(58) Field of Classification Search
None
See application file for complete search history.

(56) References Cited

U.S. PATENT DOCUMENTS

| 5,558,852 A | 9/1996 | Bigner et al. |
| 8,574,580 B2 * | 11/2013 | Silva Gonzalez ..... C07K 16/28 424/141.1 |
| 2013/0189272 A1 | 7/2013 | Grasso et al. |

FOREIGN PATENT DOCUMENTS

| EP | 2690112 A1 | 1/2014 |
| WO | WO 89/11299 | 11/1989 |
| WO | WO 93/16185 | 8/1993 |
| WO | WO 2013/163431 A1 | 10/2013 |
| WO | WO 2014/186364 A2 | 11/2014 |

OTHER PUBLICATIONS

Koivunen and Krogsrud (Labmedicine, 2006, 37:490-497).*
Barbet J. et al. (2012) Radiolabeled Antibodies for Cancer Imaging and Therapy. In: Chames P. (eds) Antibody Engineering. Methods in Molecular Biology (Methods and Protocols), vol. 907. Humana Press, Totowa, NJ.*
Gallo J, Garcia I, Padro D, et al., Journal of Materials Chemistry, 2010; 20, pp. 10010-10020.
International Search Report and Written Opinion in corresponding PCT Application No. PCT/EP2015/080349, dated Apr. 11, 2016.
Extended European Search Report in corresponding European Application No. 14382545.3 dated May 28, 2015.
Del Valle I et al: "Characterization of novel monoclonal antibodies able to identify neurogenic niches and arrest neurosphere proliferation and differentiation", Neuroscience, New York, NY, us, vol. 169, No. 3, 24 Apr. 1, 2010 (Apr. 24, 2010), pp. 1473-1485.
Elvira Gema et al: 'Targeting neural stem cells with titanium dioxide nanoparticles coupled to specific monoclonal antibodies', Journal of Biomaterials Applications, Technomic, Lancaster, PA, US, vol. 26, No. 8, May 1, 2012 (May 1, 2012), pp. 1069-1089.

(Continued)

Primary Examiner — Laura B Goddard
(74) Attorney, Agent, or Firm — Leason Ellis LLP

(57) ABSTRACT

The invention relates to the use of the monoclonal antibody NILO1 for the diagnosis, treatment and/or prevention of brain tumors and lesions. Particularly, the invention relates to methods for the diagnosis of brain tumors and brain lesions in which cells marked with said antibody, or with immunologically active fragments thereof, are detected. The invention also relates to the use of said monoclonal antibody, or immunologically active fragments thereof, as a medicament for the treatment and/or prevention of brain tumors and brain lesions. In a preferred embodiment of the invention, the monoclonal antibody NILO1, or its immunologically active fragments, are humanized.

8 Claims, 14 Drawing Sheets

(56) References Cited

OTHER PUBLICATIONS

G. Alonso, et al., Tangential Migration of Young Neurons Arising From the Subventricular Zone of Adult Rats Is Impaired by Surgical Lesions Passing Through Their Natural Migratory Pathway, The Journal of Comparative Neurology, vol. 405, pp. 508-528 (1999).
Arvidsson A, Collin T, Kirik D, et al., Neuronal replacement from endogenous precursors in the adult brain after stroke, Nat Med. 2002; 8:963-970.
Elvira G, Garcia I, Benito M, et al., Live Imaging of Mouse Endogenous Neural Progenitors Migrating in Response to an Induced Tumor, PLoS One, Sep. 2012; vol. 7, pp. e44466.
Fiona Doetsch, et al., Subventricular Zone Astrocytes Are Neural Stem Cells in the Adult Mammalian Brain, Cell, vol. 97, Jun. 11, 1999, pp. 703-716.

\* cited by examiner

MONOCLONAL ANTIBODY FOR THE DIAGNOSIS, TREATMENT AND/OR PREVENTION OF BRAIN TUMORS AND BRAIN LESIONS

CROSS-REFERENCE TO RELATED PATENT APPLICATIONS

This application is a U.S. National Phase Application under 35 U.S.C. § 371 of International Patent Application No. PCT/EP2015/080349, filed Dec. 17, 2015, and claims the priority of EP 14382545.3, filed Dec. 19, 2014, all of which are incorporated by reference in their entireties. The International Application was published on Jun. 23, 2016 as International Publication No. WO/2016/097213.

FIELD OF THE INVENTION

The present invention relates to a monoclonal antibody useful for the diagnosis, treatment and/or prevention of brain tumors and lesions. Particularly, the invention relates to methods for the diagnosis of brain tumors and brain lesions in which cells marked with said antibody, or with immunologically active fragments thereof, are detected. The invention also relates to the use of said monoclonal antibody, or immunologically active fragments thereof, as a medicament for the treatment and/or prevention of brain tumors and brain lesions. Thus, the present invention belongs to the fields of oncology, regenerative medicine and neurobiology.

BACKGROUND ART

Neural stem cells are mainly restricted to specific niches which in rodents are the subventricular zone (SVZ) in the lateral ventricles and the subgranular zone (SGZ) in the hippocampal dentate gyrus [Doetsch F, Caille I, Lim D A, et al., Cell. 1999; 97:703-716]. In the adults, type B cells express glial markers, have astrocyte characteristics, bundles of intermediate filaments and multiple processes and generate neuroblasts (type A cells, neuronal precursors) through a highly proliferative transit amplifying population (type C cells). The cell bodies of type B astrocytes are generally located under the ependymal layer of the lateral ventricles, have short processes that extend through it, with small apical endings on the ventricle, in addition to frequently tangentially oriented long basal processes with specialized end feet on blood vessels. Thus, adult SVZ B cells, similarly to the radial glia (RG) during development, retain an apical-basal polarity and are part of the ventricular epithelium. In fact, although the radial glia disappears postnatally by transformation into parenchymal astrocytes, some radial glial cells persist within the adult SVZ hidden among astrocytes of the glial tubes. This modified radial glia belongs to the astroglial lineage (type B cells) and maintains self-renewal potential and pluripotency, the two stem cell characteristics.

It is well documented the migration of adult neuroblasts in a pathway known as rostral migratory stream (RMS), in longitudinal clusters from their SVZ niche towards the olfactory bulb (OB), where dying neurons should be replaced. In addition, migration of cells from SVZ towards non-olfactory bulb regions in the adult has been reported on several disease or injury models [Arvidsson A, Collin T, Kirik D, et al., Nat Med. 2002; 8:963-970]. Surgical RMS disruption led to migration of BdrU$^+$PSA-NCAM$^+$ cells from the SVZ into the anterior olfactory nucleus, the frontal cortex and the striatum [Alonso G, Prieto M, Chauvet N., J Comp Neurol. 1999; 405:508-528]. In addition, in response to an induced brain tumor, the migration of endogenous neuroblasts towards the lesion site could be followed in vivo by magnetic resonance imaging (MRI) [Elvira G, Garcia I, Benito M, et al., PLoS One. 2012; 7:e44466].

Although DCX$^+$ neuroblasts are thought to be the major migratory SVZ cells, type C cells might migrate as well. Many of the migration experiments have been done using BrdU-labeled cells, where some, but not all the labeled cells were neuroblasts. Indeed, several reports suggest that other precursor cells from the SVZ are able to migrate towards a brain lesion site. For instance, on transgenic mice expressing a nestin driven green fluorescent protein (GFP), in response to a glioblastoma, the GFP$^+$ cells surrounding the brain tumor were actively dividing (Ki67$^+$), mushashi$^+$, glial precursors (NG2$^+$), GFAP$^+$, PSA-NCAM$^+$ or DCX$^+$. These phenotypes at the lesion site are compatible with the migration of committed and non-committed precursors. Time-lapse experiments showed that among the nestin-GFP$^+$ cells in the SVZ, there were type C cells, GFAP$^+$ cells, neuroblasts, ependymal cells and microglia, where a high percentage of motile nestin-GFP$^+$ cells were DCX$^-$. Taken together, these data suggest that DCX$^+$ neuroblasts do not represent the only motile SVZ-derived cells in the postnatal mouse brain. In cortical injuries, NG2$^+$ cells, Nestin$^+$ GFAP$^+$ cells or SVZ cells able to differentiate into glia were identified in the vicinity of the lesion site at different time points.

Despite years of intensive investigation, the diagnosis and prognosis for most patients with brain tumors or brain lesions remains poor. Median survival for adults with the most common form of brain tumor, the glioblastoma, is 8-12 months. Furthermore, most brain tumors are highly resistant to currently available therapies.

Thus, methods and compositions for prognosis, diagnosis and treatment of brain cancer have been developed which involve the use of antibodies, for instance those disclosed in WO2014186364 or WO2013163431. Specifically, US2013189272 and U.S. Pat. No. 5,558,852 refer to the use of monoclonal antibodies for the diagnosis and treatment of brain cancer. On the other hand, WO8911299 refers to a method for delivery of therapeutic agents to target brain tissue using monoclonal antibody conjugates.

The classification of brain tumors is associated with the cell type from which they arise. Astrocytes, oligodendrocytes, glial cells, may give rise to brain tumors. The presence of markers associated with these cell types may help to define the different tumor types. Neural tumors could derive from early stages of maturation rather than from neural mature cell types. Therefore, the stage at which the tumor is activated must be considered together with the origin of the cell type.

Standard treatment of brain cancer includes surgery, radiotherapy and drug selective chemotherapy. Unfortunately none of these treatments separately or in combinations is effective enough. Actually, high levels of stem cells in the resilient population correlate with a bad prognosis after therapy.

Finally, clinical evidences support the finding that some low-grade astrocytomas become more aggressive, evolving to high-grade tumors. Nevertheless, there are no markers defining this subset of tumors.

Currently there is a convincing cluster of data suggesting that some cancer cells derive from their precursor cells, which normally develop to mature cells to form individual organs.

Recently, a large number of evidence has demonstrated the presence of specific subpopulations of tumor cells directly involved in the initiation and maintenance of tumors. Defined as "cancer stem cells", their presence inside tumors is a strong indication of the metastatic capacity of a tumor and its aggressiveness. In fact, one of the major evidences of the presence of tumor initiating-cells (TICs) in solid tumors was found in aggressive brain tumors such as glioblastomas (GBM). Glioblastoma belongs to the group of fast-growing glioma tumors, with a severe prognostic and a life expectancy no longer than 24 months. There are no alternative therapies described for these tumors. GBM develops from astrocytes/glial cells and is classified as a grade IV astrocytoma. These are the most invasive type of glial tumors, rapidly growing and commonly spreading to nearby brain tissue. Sometimes, they evolve from a low-grade astrocytoma or an oligodendroglioma. GBM is a devastating brain cancer that typically results in death within 15 months after diagnosis.

Today, only sophisticated imaging techniques can pinpoint brain tumors. Diagnostic tools include computed tomography (CT or CAT scan) and magnetic resonance imaging (MRI). Intra-operative MRI also is used during surgery to guide tissue biopsies and tumor removal. Magnetic resonance spectroscopy (MRS) could help to examine the tumor's profile and determine the nature of the lesions seen on the MRI. Positron emission tomography (PET scan) can help to detect recurring brain tumors.

After brain tumor detection on a CT or MRI scan, a neurosurgeon obtains tumor tissue for a biopsy. The pathological analysis of tumor tissue should assign the tumor name and grade, providing answers about the type cell from where the tumor arise, (vg., astrocytomas arise from astrocytes) and to determine the treatment options and information about prognosis. The genetic abnormalities detected (amplification of the EGFR gene (7p12), mutations in the TP53 gene (17p13.1), loss of chromosome 10) vary depending on the nature of the tumor: primary glioblastoma (de novo) or a secondary glioblastoma (developing from a benign astrocytic tumor).

Recently, derivation of in vitro human tumor neurospheres from GBM and other aggressive brain tumors open the possibility to study cancer initiating cells.

Finally, brain tumors are not being precisely defined since there are not accurate biomarkers available. Hence the validation of new markers that allows an early and better diagnostic is a challenge. On the other hand there is not an efficient therapy for high-grade brain tumors. The first-line treatment is usually surgery, either to confirm the diagnosis with a biopsy or to remove as much of the tumor as possible. Complete resection is rarely feasible, since tumor cells usually infiltrate the surrounding brain tissue. Treatment is then completed with radiotherapy targeted at the tumor bed, combined with chemotherapy (nitrosoureas or temozolamide). In terms of survival, the benefits from adjuvant treatments after surgery are significant, although they remain modest. In case of relapse, second-line chemotherapy or reoperation may be performed. Multidisciplinary teams should carry out management of glioblastoma patients with expertise in neuro-oncology within prospective studies aiming to improve patient survival and quality of life. Prognosis is poor, especially in the absence of gross total resection, in older patients and in case of severe neurological deficits.

According to the above, alternative approaches to those currently existing are needed for an early and more accurate identification of brain damages, including tumors. Moreover, a need exists for an effective way to deliver therapeutic agents specifically in the damaged site in order to treat brain injuries. Such site-directed drug delivery systems would allow a reduction in the doses needed of the drug, since they could exert their therapeutic action directly in the damaged zone.

DESCRIPTION OF THE INVENTION

This invention proposes the use of NILO1, a previously characterized monoclonal antibody (mAb) that identifies early neural progenitors in the SVZ niche (EP2690112A1), for the early diagnosis and/or prognosis of brain tumors and brain lesions.

Type B astrocytes are among the SVZ-derived cell types able to migrate in response to a damage insult. The present invention demonstrates that NILO1$^+$ cells show an immunophenotype and subependymal localization compatible with B astrocytes. Thus, the detection of cells positively marked with NILO1 allows the identification of B astrocytes migrating towards the lesion site, which is a trait shared by different brain injuries in the adult brain.

The present invention shows that the mAb called NILO1 is able to identify surface antigens in type B astrocytes and radial glia during development. Thus, this antibody allows the identification of adult neural stem cells, not only in their niches, but also during their fast and orderly migration towards a lesion site in vivo, for instance using MRI, or in vitro. Furthermore, the migration of these cells towards a lesion site is a general trait that can be detected for example during development of a tumor, following a cryolesion, demyelination or even a mechanical injury.

Neuroblasts represent the predominant migrating cell type in the adult brain. There are, however, increasing evidences of migration of other neural precursors. This invention shows the identification in vivo and in vitro of endogenous early neural precursors, different from neuroblasts, able to migrate in response to brain injuries. The examples of the present invention show in living mice that mAb NILO1, which unequivocally identifies type-B astrocytes and embryonic radial glia, allowed the in vivo identification of endogenous type-B astrocytes at their niche, as well as their migration to the lesion site in response to glioblastoma, demyelination, cryolesion or mechanical injuries. In addition, NILO1$^+$ adult radial glia-like structures were identified at the lesion site a few hours after damage. For all damage models used, type-B astrocyte migration was fast and orderly. Identification of NILO1$^+$ cells surrounding an induced glioblastoma was also possible after intraperitoneal injection of the antibody. This allows an early identification of the damage site(s) after brain insults, by the detection of type-B astrocytes labeled with NILO1.

On the other hand, the mAb NILO1 is capable of binding human tumoral cell antigens (see FIG. 1E) and blocking the proliferation of said tumoral cells, so that it is useful for the detection (diagnosis) and treatment of brain tumors, preferably glioblastoma.

NILO1 is also useful as a medicament for the treatment of brain tumors and brain lesions. Due to its specificity to tumoral cells, and taking into account that the antibody binds type-B astrocytes which are migrating to the damaged area, said antibody may act alone or may be bound to active principles or therapeutic particles and acts as a drug delivery system specifically in the damaged site.

Thus, a first aspect of the present invention relates to the use of the monoclonal antibody, called NILO1, produced by the hybridoma deposited under the DSM access number No.

ACC2887, or an immunologically active fragment thereof, for the manufacture of a reactive for the diagnosis of brain tumors and lesions. Alternatively, this invention relates to the use the monoclonal antibody, called NILO1, produced by the hybridoma deposited under the DSM access number No. ACC2887, or an immunologically active fragment thereof, as a reactive for the diagnosis of brain tumors and lesions.

The monoclonal antibody NILO1, produced by the hybridoma deposited under the DSM access number No. ACC2887, is disclosed in EP2690112A1. In the present invention this monoclonal antibody NILO1 will be also called "mAb NILO1" or "NILO1".

The "immunologically active fragments of antibodies" comprise at least part of a full length antibody, said part being the antigen binding region or variable region thereof. Examples of "immunologically active fragments of antibodies" include the Fab, Fab', F (ab')2 and Fv fragments; diabodies; linear antibodies or single chain antibody molecules. Several techniques have been developed to produce fragments of antibodies. Traditionally, these fragments come from the proteolytic digestion of intact antibodies. However, these fragments can now be produced directly by means of recombinant host cells. For example, the fragments of antibodies can be isolated from the libraries of antibody phages. Alternatively, the Fab'-SH fragments can be directly recovered from a host cell expressing them and chemically bound to form F(ab')2 fragments. In another embodiment, the F(ab')2 is formed using the leucine zip GCN4 to promote the assembly of the F(ab')2 molecule. In accordance with another approach, the F(ab')2 fragments of the recombinant host cell culture can be directly isolated. Other techniques for the production of fragments of antibodies shall be evident for persons skilled in the art. In other embodiments, the chosen antibody is a single chain Fv fragment (scFv). For a revision, see WO1993016185.

The "fragments of antibodies" may comprise the VH and VL domains of the antibody, wherein these domains are present in a single polypeptide chain. In general, the Fv polypeptide further comprises a polypeptide setting between the VH and VL domains which enables the desired structure for the antigen binding to be formed.

In the present invention, the immunologically active fragments of the antibody are capable of specifically recognizing an epitope in the cell surface recognized by the full length monoclonal antibody Nilo1.

The term "diabodies" relates to small fragments of antibodies with two antigen binding sites, these fragments comprising a heavy chain variable domain (VH) connected to a light chain variable domain (VL) in the same polypeptide chain. Using a setting that is too short to allow the two domains to pair in the same chain, the domains are forced to pair up with the complementary domains of another chain and create two antigen binding sites.

The expression "linear antibodies" relates to antibodies comprising a pair of tandem segments Fd (VH-CH 1-VH-CH 1) which form a pair of antigen binding regions. The linear antibodies may be bispecific or monospecific.

The term "diagnosis" refers to the process performed in order to identify the presence or absence of a pathological condition, particularly brain tumors or brain lesions, in a subject, preferably human. The term "prognosis" refers to the process performed in order to predict the events that will occur during the curse of a pathological condition, particularly brain tumors or brain lesions, more preferably brain tumor, including without limitation relapse, metastasis or response to a treatment.

In a preferred embodiment, the mAb NILO1 or the immunologically active fragment thereof is coupled to a support or a particle, preferably nanoparticle, more preferably magnetic nanoparticle, more preferably magnetic glyconanoparticle, even more preferably wherein said nanoparticle further comprises a G protein immobilized in its surface.

The term "support", as used herein, refers to any surface to which the mAb NILO1 or the immunologically active fragment thereof may be attached without losing their antigen binding properties. Preferably, said support may be a matrix, for instance a nylon matrix, a plate, beads (for instance spherical beads, which may be made of agarose or biodegradable matrixes, they also may be magnetic spherical beads). This support may be made of any material which allows the maintenance of the antigen binding properties of the mAb NILO1 or the immunologically active fragment thereof, such as silicon, graphene or glass.

The term "particle" means any particle made or coated of any material that preferably may be excited and/or activated, such as gold, graphene, titanium oxide or silicon oxide.

The term "nanoparticle" (NP) refers to a microscopic particle with nanometric size, preferably lesser than 100 nm, more preferably lesser than 10 nm.

The term "magnetic nanoparticle" refers to a nanoparticle which has a magnetic core, for instance, but without limitation, comprising Fe, more preferably comprising $Fe_3O_4$.

The term "glyconanoparticle" means a nanoparticle composed of carbohydrate, typically of a glycan.

The attachment of the mAb NILO1 or the immunologically active fragment thereof to a support or a particle facilities the implementation of the same in any standard equipment for the detection of antigen-antibody interactions.

The detection of antigen-antibody interactions in the present invention may be performed by means of any technique allowing the recognition of the mAb Nilo1 or immunologically active fragments thereof. In a more preferred embodiment, the diagnosis of brain tumors and lesions in the present invention by means of NILO1 or immunologocally active fragments thereof is performed by magnetic resonance imaging, flow cytometry, immunohistochemistry, ELISA, and/or Western Blot, or by any other positive selection method.

A "brain lesion", as used herein, is an area of tissue within the brain that has been damaged through injury or disease. They may occur in different locations. Brain lesions can be caused by injury, infection, exposure to certain chemicals, problems with the immune system, etc. They also may be caused by abscesses, arteriovenous malformations, cerebral infarction, multiple sclerosis, neurodegenerative process, demyelination, mechanical injury, cryolesion or stroke, among others.

A "brain tumor" or "intracranial neoplasm" is associated to the presence of abnormal cells within the brain or any other tissue within the nervous system. The present invention refers to both type of tumors, malignant or cancerous tumors and benign tumors, as well as low grade-tumors or high grade tumors. Cancerous tumors can be divided into primary tumors that started within the brain and those that spread from somewhere else known as brain metastasis tumors. The most common primary brain tumors are, without limitations, gliomas, meningiomas, pituitary adenomas, nerve sheath tumors. The brain tumor referred to in the present invention is, preferably, pilocytic astrocytoma, glioblastoma, oligodendroglioma, ependymoma, medulloblastoma or meningioma. As used herein, the term "brain tumor" includes any "nerve tumor", also called "tumor of the nervous system" or "nervous system neoplasm", which can be formed in the peripheral nerve network anywhere in the body. These nerve tumors often affect the function of the nerve, causing pain and disability. There are three major categories of nerve tumors, which are included within the scope of the present invention, they are neurofibroma, schwannoma or malignant peripheral nerve sheath tumor, among others.

In an even more preferred embodiment, the brain lesion is produced by a neurodegenerative process, demyelination, mechanical injury, cryolesion or stroke, and the brain tumor is glioblastoma.

Another aspect of the invention refers to the mAb NILO1, or an immunologically active fragment thereof, for use as a medicament.

The "medicament" of the present invention may be for human or veterinary use. The medicament for human use is any substance or combination thereof which has properties in the treatment or prevention of pathological conditions in human beings or that may be administered to humans in order to restore damaged or impaired physiological conditions, exerting pharmacological, immunological or metabolic actions. The medicament for veterinary use is any substance or combination thereof which has properties in the treatment or prevention of pathological conditions in non-human animals or that may be administered to non-human animals in order to restore damaged or impaired physiological conditions, exerting pharmacological, immunological or metabolic actions.

Another aspect of the invention refers to the mAb NILO1, or an immunologically active fragment thereof, for use in the treatment and/or prevention of brain tumors or lesions, preferably wherein the brain lesion is produced by a neurodegenerative process, demyelination, mechanical injury or stroke, and the brain tumor is glioblastoma.

The term "treatment" refers to the process carried out in order to fight against the effects caused by a pathological condition, preferably brain tumors or lesions, in a subject, preferably human.

The term "prevention" refers to the process carried out in order to avoid the onset of a pathological condition, preferably brain tumors or lesions, in a subject, preferably human, particularly when said subject is predisposed to suffer the pathological condition even though he has not been diagnosed yet.

In a preferred embodiment, the mAb NILO1 or said fragment is coupled to an active principle and/or a particle, wherein preferably the active principle is a drug, and more preferably the particle is a nanoparticle, more preferably magnetic nanoparticle, more preferably magnetic glyco-nanoparticle, even more preferably wherein said nanoparticle further comprises a G protein immobilized in its surface.

As used herein, the term "active principle", "active substance", "pharmacologically active substance", "active ingredient" or "pharmacologically active ingredient" means any substance that provides a pharmacological activity in the mitigation, treatment or prevention of a pathological condition. This term includes those components that lead to a chemical change during drug manufacturing. This term includes drugs and pro-drugs.

In a more preferred embodiment, the active principle is for the treatment and/or prevention of brain tumors and lesions, preferably wherein the brain lesion is produced by a neurodegenerative process, demyelination, mechanical injury or stroke, and the brain tumor is glioblastoma.

When the mAb NILO1 or the immunologically active fragment thereof is coupled to an active principle and/or a particle it can be used as a drug delivery system in the damaged brain area, since as explained above, it is capable of binding neural cells that are migrating to the lesion region or tumoral cells.

A "drug delivery system" refers to approaches, formulations, technologies, and systems for transporting an active principle in the body as needed to safely achieve its desired therapeutic effect in a site-specific manner. It involves site-targeting within the body, or it might involve facilitating systemic pharmacokinetics; in any case, it is concerned with both quantity and duration of drug presence. Thus, in another preferred aspect, the mAb NILO1 or the immunologically active fragment thereof is used as a drug delivery system, preferably for the treatment and/or prevention of brain tumors and brain lesions, preferably wherein the brain lesion is produced by a neurodegenerative process, demyelination, mechanical injury or stroke, and the brain tumor is glioblastoma.

In an even more preferred embodiment, the mAb NILO1 or the immunologically active fragment thereof is humanized.

In most cases, the "humanized antibodies" are human immunoglobulins (receptor antibodies) wherein the residues of the hypervariable regions of the receptor have been substituted by residues of a hypervariable region of a non-human species (donor antibody) such as mouse, hamster, rat, rabbit or a non-human primate which has the desired specificity, affinity and capacity. Thus, in the present invention the humanized antibody or immunologically active fragment thereof humanized is or derive from human immunoglobulins wherein the residues of the hypervariable regions have been substituted by residues of the hypervariable region of the mAb NILO1.

In some cases, the framework residues (FR) of the Fv region of human immunoglobulin are substituted by the corresponding non-human residues. Furthermore, the humanized antibodies may comprise residues not found in the receptor antibody or in the donor antibody. These modifications are performed to further refine antibody function. In general, the humanized antibody shall substantially comprise all of at least one, and generally two, variable domains, wherein all or practically all of the hypervariable loops correspond to those of a non-human immunoglobulin and all or substantially all the FR regions are those of a sequence of human immunoglobulin. The humanized antibody will also optionally comprise at least part of a constant region of the immunoglobulin (Fc), in general of a human immunoglobulin. Different processes to obtain humanized antibodies are known in the state of the art.

Another aspect of the present invention refers to a method for the in vitro diagnosis of brain injuries, preferably brain tumors, more preferably glioblastoma, hereinafter "first method of the invention", which comprises:

a. Putting in contact an isolated biological sample with the mAb NILO1, or an immunologically active fragment thereof, b. detecting, preferably by flow cytometry, immunohistochemistry, ELISA, and/or Western Blot, the presence of cells marked with the antibody or an immunologically active fragment thereof, and c. associate the presence of said cells to a brain injury, preferably to a brain tumor.

The term "isolated biological sample" refers to any sample obtained from any tissue or fluid of a subject, which may be obtained by any method known in the field. The biological sample may be a tissue or fluid sample obtained preferably from the brain. More preferably the biological sample, as described in the present invention, is obtained from one or more areas of the brain outside the neural stem cells niche. Alternatively, it may be a blood, plasma, serum, lymph, urine, cerebrospinal fluid, mucus, sputum, tears, etc. sample. Said biological sample may be obtained from a human, or a non-human mammal, such as dogs, cats, rodents, ruminants, etc. In a more preferred embodiment, the isolated biological sample derives from a mammal, even more preferably the isolated biological sample derives from a human.

Another aspect of the present invention refers to a method for obtaining data for the diagnosis of a brain tumor or lesion, preferably brain lesions produced by a neurodegenerative process, demyelination, mechanical injury or stroke, hereinafter "second method of the invention", which comprises:

a. detecting the presence of cells marked with the mAb NILO1, or an immunologically active fragment thereof, in the brain or in an isolated biological sample from brain, of a subject previously injected with said antibody or an immunologically active fragment thereof, wherein the step (a) is preferably performed by magnetic resonance imaging, flow cytometry, immunohistochemistry, ELISA, and/or Western Blot, more preferably by magnetic resonance imaging.

The subject has been previously injected preferably intraperitoneally with said antibody or an immunologically active fragment thereof.

In a preferred embodiment of the first and second method of the invention, the mAb NILO1 or the immunologically active fragment thereof, is coupled to a support or a particle, preferably nanoparticle, more preferably wherein the magnetic nanoparticle is a magnetic glyconanoparticle, more preferably wherein said nanoparticle further comprises a G protein immobilized in its surface.

Another aspect of the present invention refers to the mAb NILO1, or an immunologically active fragment thereof, coupled to a support, an active principle and/or a particle, wherein preferably the active principle is a drug and more preferably the particle is a nanoparticle, more preferably magnetic nanoparticle, more preferably magnetic glyconanoparticle, even more preferably wherein said nanoparticle further comprises a G protein immobilized in its surface.

In a preferred embodiment, the active principle is for the treatment and/or prevention of brain tumors or lesions, preferably wherein the brain lesion is produced by a neurodegenerative process, demyelination, mechanical injury or stroke, and the brain tumor is glioblastoma.

In a more preferred embodiment, the mAb NILO1 or the immunologically active fragment thereof is humanized.

The mAb NILO1 or the immunologically active fragment thereof as described in the present invention may be "marked", preferably when it is used in the first or second method described herein. The term "marked" means that the mAb NILO1 or the immunologically active fragment thereof is bound to a label. Labels that can be bound to an antibody are known in the art, for instance, radioisotopes (such as 32P, 35S or 3H), fluorescent or luminiscent labels (such as green fluorescent protein (GFP), fluoresceine (FITC), rhodamine, texas red, phycoerythrin (PE), allophycocyanin, 6-carboxyfluorescein (6-FAM), 5(6)-carboxy-X-rhodamine (ROX), 5-carboxyfluorescein (5-FAM)), secondary antibodies or fragments thereof, affinity labels (such as biotin, avidin, agarose, Bone Morphogenetic Proteins (BMPs) or haptens), enzymes or enzyme substrates (such as alkaline phosphatase (AP) or Horseradish peroxidase (HRP)).

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples, drawings are provided by way of illustration and are not intended to be limiting of the present invention.

EXAMPLES

1. Materials and Methods 1.1. Animals

Figure 1:
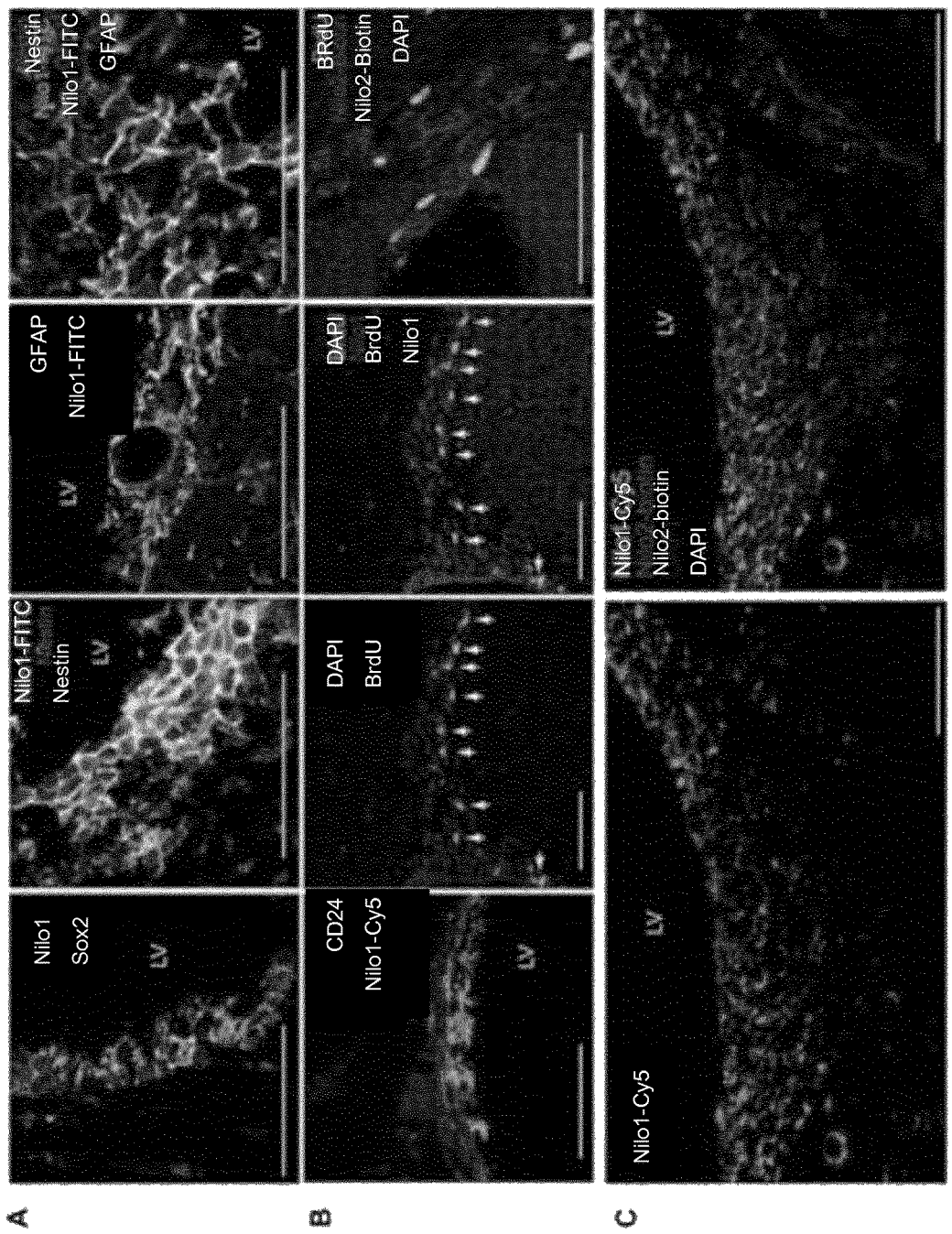
FIG. 1. Nilo1 mAb identifies type B astrocytes in the adult brain, as well as embryonic radial glia. Immunohistochemistry of subventricular zone from wild type mice by confocal microscopy showing A, double staining with Nilo1 and Sox2, Nestin, GFAP or a triple labeling Nilo1, GFAP and Nestin, indicating that the Nilo1$^+$ cells are positive for these markers. B, Nilo1$^+$ cells are CD24$^-$ and had a sub-ependymal localization. Cells labeled with a short pulse of BrdU (50 mg/kg, 1 h before sacrifice) expressing high levels of Pax6 (see arrows), corresponding to the C population, are different from Nilo1$^+$ cells (middle panels) and from neuroblasts (Nilo2$^+$ cells, right panel). C, Double staining with Nilo1 and Nilo2 demonstrating that Nilo1$^+$ cells are different form Nilo2$^+$ cells (neuroblasts). D, Immunohistochemistry of fixed brains (telencephalic cortex) from E10 mouse embryos double stained with Nilo1 and either nestin or vimentin. Nuclei were counterstained with DAPI. LV, lateral ventricle. V, ventricle. P, pial suface. Scale bars: 50 μm. E, human primary glioblastoma growing in vitro as neurospheres was stained with Nilo1 mAb and revealed with a secondary FITC mouse IgG anti-hamster Ig (left) and counterstained with DAPI (middle). The merged picture is seen on the right panel.
Figure 1:
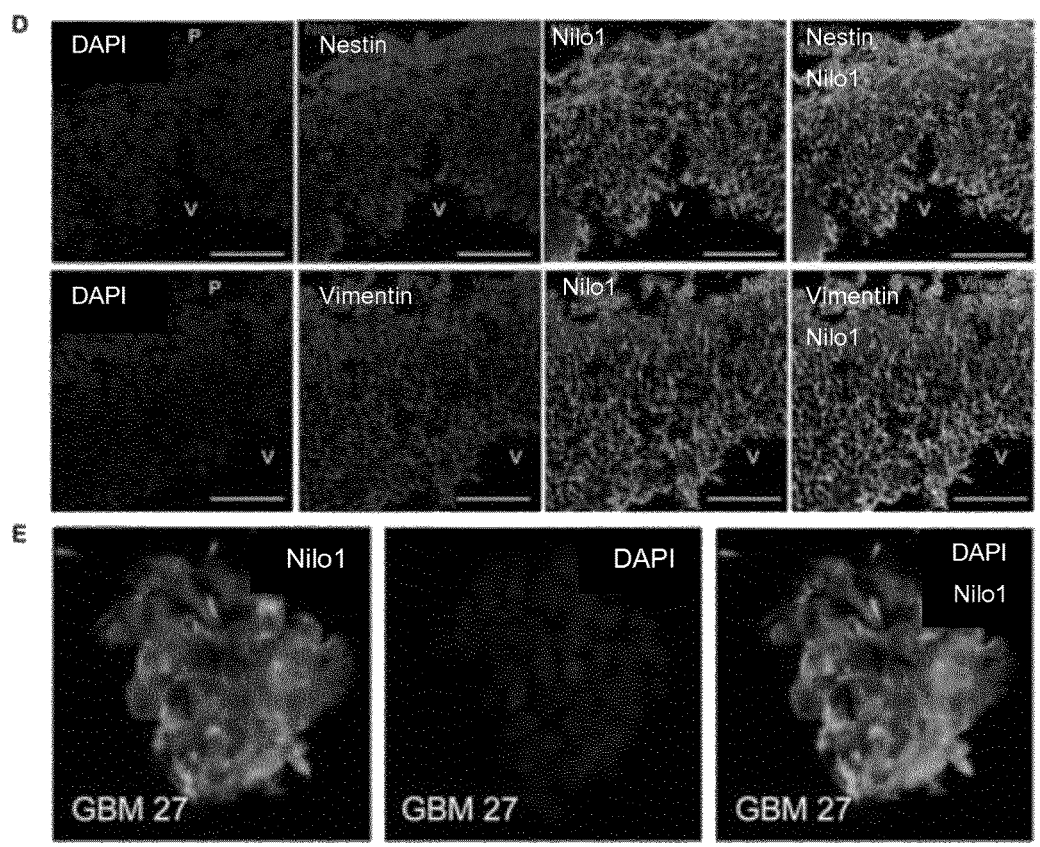

For these experiments, 6-8 weeks old C57Bl/6J 103 mice (males), bred and housed under standard conditions were used.

1.2. Antibodies

Nilo1 mAb was generated by the fusion of hamster B cells and the mouse myeloma X63Ag8, as described [EP2690112A1]. Purification of Nilo1, biotinylation and Cy5 labeling was from ProteinTools (CNB-CSIC, Madrid, Spain).

1.3. Characterization of the Protein G-Magnetic Glyconanoparticles (mGNPs) and Coupling to Nilo1

Water-soluble magnetic glyconanoparticles, consisting on a magnetic core (4 nm of diameter) covered with a 1 nm gold shell and coated with carbohydrates and an amphiphilic linker ended in a carboxyl group, were prepared and characterized as previously described [Gallo J, Garcia I, Padro D, et al., J. Mat. Chem. 2010; 20:10010]. Recombinant protein G was covalently immobilized to these particles, which enabled the subsequent capture of IgG antibodies.

Characterization of Protein G-glyconanoparticles (mGNPs) including size and T2* estimation was made as described [Elvira G, Garcia I, Benito M, et al., PLoS One. 2012; 7:e44466]. mGNPs (100 µg) were incubated 5 h at 4° C. with Nilo1 mAb (135 µg) in 0.1 M glycine buffer pH 9.0 on a final volume of 50 µl.

Characterization of the amount and functionality of the coupled antibody was made as described [Elvira G, Garcia I, Benito M, et al., PLoS One. 2012; 7:e44466].

1.4. Cell Culture

CT-2A mouse astrocytoma (a gift from Prof. T. N. Seyfried, Boston, Mass., USA), and GFP-CT-2A (a gift from A. Martinez, I. Cajal, CSIC, Madrid, Spain), were grown in RPMI medium, 10% heat-inactivated fetal bovine serum in 5% $CO_2$ at 37° C. and 95% humidity.

1.5. Isolation and Culture of Cancer-Initiating Cells from Human Glioblastoma Samples Glioblastoma (GBM) Tumor Stem Cells were isolated from 4 different human fresh GBM samples. Tissue samples were obtained from patients operated at the Neurosurgery department, Hospital la Fe, Spain.

GBM Tumor Stem Cells were cultured in media containing: DMEM/F-12 (Gibco, 11039021) with Non Essential Amino Acids (10 mM; Gibco, 11140), Hepes (1M; Gibco, 15630), D-Glucose 45% (Sigma, G8769), BSA-F5 7.5% (Gibco, 15260), Sodium Pyruvate (100 mM; Gibco, 11360), L-Glutamine (200 mM; Gibco), Antibiotic-Antimycotic (100×; Gibco, 15240), N-2 Supplement (100×; Gibco, 17502), Hydrocortisone (1 µg/µl; Sigma, H0135), Tri-iodothyronine (100 µg/ml; Sigma, T5516), EGF (50 ng/µl; Sigma, E9644), bFGF (25 ng/µl; Sigma, F0291) and Heparin (1 ng/µl).

1.6. Surgical Procedures

Mice were anaesthetized intraperitoneally with 100 mg/Kg of ketamine and 10 mg/Kg of xylacine, their heads were immobilized on a stereotaxic frame and intracranially injected with 1 µl of Nilo1-mGNPs in the right striatum at coordinates +0.9 mm anterior, +0.75 mm lateral, −2.75 mm ventral from bregma point. In control animals, PBS buffer was injected.

Brain fixations were performed on anesthetized mice by transcardiac perfusion with 4% paraformaldehyde (PF) in 0.1 M phosphate buffer (fixation buffer). Brains were extracted and post-fixed overnight at 4° C. in fixation buffer and cryoprotected in fixation buffer with 30% sucrose for two days at 4° C. before freezing at −80° C. Fixed brains were cut with a cryostat (25 µm thick) and slices were maintained at −20° C. in 30% (v/v) glicerol, 30% (v/v) etilenglicol, PB 0.1M pH 7.4 until analyzed.

Tumors were generated by grafting $10^2$-$2 \times 10^5$ CT-2A (or GFP-CT-2A) cells intracranially at stereotaxic coordinates +0.1 mm anterior, −2.25 mm lateral, −2.70 mm ventral into the right caudate putamen, in 1 µl of PBS (n=6 for MRI analyses).

Demyelination was induced by injecting 1 µl of 2% LPC in PBS near the corpus callosum, at stereotaxic positions +1 mm anterior, −1 mm lateral, −2 mm ventral from bregma point, on anaesthetized mice. Mice (n=6) were sacrificed 7 or 25 days later.

Mechanical injuries were made on anaesthesized mice by inserting a Hamilton needle by stereotaxic surgery (coordinates +0.9 mm anterior, +0.9 mm lateral, −2.75 mm ventral refereed to bregma point) (n=6). In some mice, the lesion site was labeled by nigrosine (0.5 µl i.c. containing 0.5 ng/µl in sterile PBS). Mice were sacrificed one to three days later.

The cryolesion was generated by applying for 10 s a dry ice pellet onto the left frontoparietal bone of anaesthetized mice. Mice (n=5) were sacrificed three days later.

1.7. Magnetic Resonance Imaging

MRI studies were performed on a Bruker Biospec 70/20 scanner using a combination of a linear coil (for transmission) with a 4-element mouse head phased array coil (for reception). Animals were anesthetized with sevofluorane (5% for induction and 2% for maintenance) and placed in an MRI-adapted stereotaxic holder. Respiration and body temperature were continuously monitored. MRI acquisition protocol included an initial flash sequence (repetition time: 100 ms, echo time: 6 ms, field of view: 4 cm, matrix: 128×128) to center the Field of View (FOV), followed by a shimming procedure applied to a region of interest covering the head (FOV=3×2×2 cm, matrix=64×64×64) based on a Field Map sequence (TR=20 ms, TE=1.43 and 5.42 ms).

As an anatomical reference, a T2-weighted axial study (TR=2500 ms; TE, 33 ms; α=180°; FOV=2×2 cm; matrix=256×256; slice thickness=0.5 mm, 15 slices to cover the whole brain) was used and nanoparticles were detected and tracked with a T2*-weighted 3D multi gradient echo (MGE) sequence (TR=200 ms; 8 echoes, TE=10 to 45 ms; echo spacing=5 ms; α=15°; FOV=1.6×1.6×1.5 cm; matrix=192×96×96).

To increase the signal-to-noise ratio (SNR) and improve image contrast, the different echo images from the MGE sequence were added (in magnitude). To display the results, the tumor area was manually segmented on the T2 axial scans and transferred to the MGE image.

1.8. Immunological Analyses and Staining Procedures

Single cells suspensions from cultured neurospheres were attached onto Matrigel Basement Membrane Matrix Growth Factor Reduced (BD Pharmingen) pre-coated coverslips with diluted in culture media (1:20 v/v) as described [Elvira G, Garcia I, Benito M, et al., PLoS One. 2012; 7:e44466]. Cells were fixed with 4% PF in PBS buffer for 15 min at RT. Quenching was performed by adding 0.1 M glycine pH 7.4 for 15 min at RT. After three PBS washes, blocking was performed by incubating the coverslips with 10% goat serum in PBS during 1 h at RT. Fixed cells were incubated overnight with Nilo1-mGNPs or purified Nilo1 mAb at 4° C. After three PBS washes, cells were incubated with anti-Ha-FITC secondary antibody 1:100 for 1 h.

To assess whether MRI signals corresponded to labeled type B astrocytes, brains from mice used in MRI analyses were fixed and cryopreserved for cryostat sectioning in a plane parallel to that of axial MR imaging. Serial 20-25 µm thick frozen sections were collected through the entire mouse brain. Anatomical landmarks such as corpus callosum, lateral ventricles opening, shape and anterior commisure of the brain were used for the spatial alignment of MRI and immunohistochemical sections.

Brain sections of wild-type mice or mice intracranially injected with Nilo1-mGNPs were blocked with 10% mouse serum in PBS during 1 h at RT and stained with the appropriate antibodies (Table 1).

TABLE 1

Commercial antibodies used in immunohistochemistry.

| Antibody | Host | Source | Clone or Cat. # | Ab Dilution |
|---|---|---|---|---|
| PRIMARY ANTIBODIES | | | | |
| SOX2 | Rabbit | Chemicon | AB5603 | 1:400 |
| DCX | Goat | Santa Cruz Biotech. | Sc-8066 | 1:200 |
| Nestin | Mouse | Chemicon | MAB353 | 1:100 |
| Biotin CD24 | Mouse | BD Pharmingen | 553260 | 1:200 |
| GFAP | Rabbit | Dako | Z0334 | 1:3000 |
| Pax6 | Rabbit | Covance | PRB278P | 1:300 |
| Anti-BrdU-FITC | Mouse | Becton Dickinson | 347583 | 1:20 |
| Biotin Ter-119 | Mouse | BD Pharmingen | 553672 | 1:200 |
| PSA-NCAM | Mouse (IgM) | Abcys online | AbC0019 | 1:1000 |
| Vimentin | Rabbit | AbCam | Ab 7783 | 1:200 |
| Oligodendrocyte 2Q92 | Mouse | AbCam | Ab 64547 | 1:1000 |
| Myelin | Mouse | Chemicon | MAB 328 | 1:1000 |
| EGFR | Rabbit | Santa Cruz Biotech. | Sc-12357-R | 1:100 |
| SECONDARY ANTIBODIES AND REAGENTS | | | | |
| BrdU | — | Sigma | B-5002 | 50 mg/kg (i.p.) |
| Anti-hamster-FITC | Mouse | BD Pharmingen | 554011 | 1:100 |
| Anti-mouse Alexa Fluor 647 | Goat | Molecular Probes | A-21235 | 1:300 |
| Anti-mouse IgG-Texas Red | Goat | Molecular Probes | T-862 | 1:400 |
| Anti-mouse IgM A488 | Goat | Molecular Probes | A-21042 | 1:400 |
| Anti-rabbit Alexa Fluor 568 | Goat | Molecular Probes | A-11011 | 1:400 |
| Anti-rabbit IgG-Cy3 | Goat | Jackson | 111-165-003 | 1:400 |
| Anti-rabbit Alexa Fluor 647 | Goat | Molecular Probes | A-21244 | 1:400 |
| Anti-goat 594 | Chicken | Invitrogen | A21468 | 1:400 |
| Anti-hamster biotin | Mouse | BD Pharmingen | 550335 | 1:100 |
| Streptavidin Texas Red | — | Molecular Probes | S-872 | 1:400 |
| Streptavidin Alexa Fluor | — | Molecular Probes | S-32354 | 1:400 |
| DAPI | — | Invitrogen | D1306 | 0.3 µM |
| Hoechst 33342 | — | Invitrogen | H3570 | 5 µg/mL |

For the identification of Nilo1⁺ cells on NILO1-mGNPs injected mice, anti-Ha-FITC (1:100) or, alternatively, anti-hamster biotin (1:100) followed by streptavidin-A488 (1:400) or streptavidin-Texas Red (1:400) were used. Coverslips were mounted with an anti-fade (Mowioll488), counterstained with either DAPI or Hoechst 33342. Images were collected with a Leica TCS-SP5-AOBS confocal microscope (Mannheim, Germany). Detection ranges were set to eliminate crosstalk between fluorophores.

For in vivo identification of Nilo1⁺ cells surrounding the brain tumor, mice were intraperitoneally injected with Nilo1 ascites at 10 µg/g of body weight one week after stereotaxic injection of 100 GFP-CT-2A cells. Mice were sacrificed 24 h later and 25 µm sections of fixed brains were analyzed using a secondary Cy5.5-labeled anti214 hamster antibody.

Short BrdU labeling in vivo. Mice were intraperitoneally injected with a single dose of BrdU (50 mg/kg). Mice were sacrificed 1 h later and 25 µm cryostate sections were collected. Fixed brain sections were denatured with 2N HCl in PBS, 0.3% Triton X-100 (PBST) during 30 min at 37° C. After PBST washes, sections were blocked with 10% goat serum in PBST and incubated with a secondary FITC-labeled anti-BrdU antibody during 24 h at 4° C. The Pax6$^{high}$ BrdU⁺ population labeled with this protocol represents the type C transit amplifying progenitors. These samples were additionally stained with Nilo1 mAb.

C57131/6 mouse embryos were obtained in E10 development stage, fixed by immersion in fixation buffer overnight at 4° C. and cryoprotected in fixation buffer with 30% sucrose for two days at 4° C. before freezing in OCT blocks. Cryostat sections of the embryos were mounted in poly-lysine slides and maintained at −20° C. until analyzed (histology service in CNB-CSIC, Madrid, Spain). Radial glia was identified by using vimentin and nestin antibodies in a Leica TCS-SP5-AOBS confocal microscope (Mannheim, Germany). Images of E10 mouse embryo used to compose overview were collected in a Leica AF6000 LX Live Cell Imaging microscope (Mannheim, Germany).

1.9. Flow Cytometry

Single cell suspensions from neurospheres were obtained after incubation with accutase (5 min, 37° C.). Unspecific antibody binding was blocked with PBS, 10% goat serum, 3% BSA, 0.0025% NaN$_3$ for 30 min at 4° C. An excess of Nilo1-mGNPs was added to the cell suspension and incubated for 1 h at 4° C. Cells with purified Nilo1 were incubated as a positive control. After PBS washes, cell suspensions were stained with anti-Ha-FITC (1:100 diluted in PBS, 5% BSA, 0.025% NaN$_3$). Following additional PBS washes, cells were resuspended in 300 µl cold PBS until FACS measurements (Epics XL, Coulter). Propidium iodine was added (25 µg/ml) to each sample to gate on living cells.

1.10. T2* MRI Signal Quantification

The accumulation of nanoparticles over time is reflected as an increase in the T2* hypointensity, equivalent to a drop in the overall intensity of the MRI signal. To evaluate the accumulation of nanoparticles, signal intensity levels in the T2*-weighted images were measured over time. For each animal, a region of interest (ROI) including the tumor area and its surroundings was manually delimited on the anatomical images (T2-weighted), at the final time point of the experiment. This ROI was translated to the T2*-weighed images (all images were previously co-registered) and the overall intensity value in the volume of interest was computed for each day of experiment on all the MRI sections. This processing was performed with the software MMWKS (Multimodality WorkStation). Signal intensity levels over time are expressed as percentage of the baseline T2* intensity for each animal and represented as mean±S.D.

2. Results 2.1. Nilo1 mAb Identifies Type B Astrocytes in the SVZ Niche

Nilo1 antibody was developed and characterized. Nilo1 was described as identifying Sox2$^+$, GFAP$^+$, vimentin$^+$, EGFR$^+$, DCX$^-$, PSA-NCAM$^-$, Tuj1$^-$ cells, suggesting that it identifies a highly undifferentiated neural precursor. It was corroborated that Nilo1 recognized Nestin$^+$, GFAP$^+$ and Sox2$^+$ at the SVZ niche (FIG. 1A). The antigen recognized by Nilo1 mAb was not expressed in ependymal cells at the wall of the lateral ventricles (CD24$^+$) (FIG. 1B). In addition, Nilo1$^+$ cells did not correspond to type C cells (identified by a short pulse of BrdU and co-expressing high levels of Pax6), since the BrdU$^+$Pax6$^{high}$ and the Nilo1$^+$ cells represented two distinct populations (FIG. 1B). As control, it is shown that a short pulse of BrdU did not label neuroblasts (FIG. 1B). Furthermore, Nilo1 did not recognize neuroblasts. Moreover, the antigenic phenotype of Nilo1$^+$ cells allowed us to exclude that they could represent either intermediate progenitors such as NG2-glia, which are GFAP$^-$, or differentiated astrocytes, since there is no Nilo1 signal in the brain cortex.

Taken together, these data indicated that Nilo1 mAb identified surface antigens in SVZ-derived type B astrocytes, defined in adult mice as neural stem cells, since Nilo1$^+$ cells i) had a subependymal localization and did not recognize ependymal CD24$^+$ cells, ii) did not represent type C cells, iii) identified a population distinct from neuroblasts, iv) did not represent differentiated astrocytes nor intermediate progenitors NG2-glia like, and v) identified SOX2$^+$, nestin$^+$ GFAP$^+$ cells. Further support to this notion came from the observation that on E10 mouse embryos, the radial glia markers vimentin and nestin identified the same cells as Nilo1 (FIG. 1 D).

In addition, Nilo1 mAb recognized surface antigens in primary human glioblastoma cell lines growing as neurospheres (FIG. 1 E). Indeed, 5 primary human glioblastoma cell lines, derived from 4 different patients, were analyzed and in all of them there were cells positively stained with Nilo1 mAb. These data indicate that this mAb is able to recognize, in addition to the mouse antigens against which they were raised, the homologous antigen in humans.

2.2. In Vivo Tracking of Nilo1$^+$ Cells Mobilized Towards an Induced Glioblastoma In order to assess whether more undifferentiated precursors (type B cells), despite neuroblasts, were also able to migrate to an induced tumor, Nilo1 mAb was coupled to mGNPs (FIG. 2A), which had been fully characterized elsewhere in terms of size core, shell composition, relaxivity and functionality. Functionality of the Nilo1-mGNPs was evaluated by flow cytometry, immunocytochemistry and immunohistochemistry of the SVZ following in vivo injection of the Nilo1-mGNP particles (FIG. 2B-D).

Figure 2:
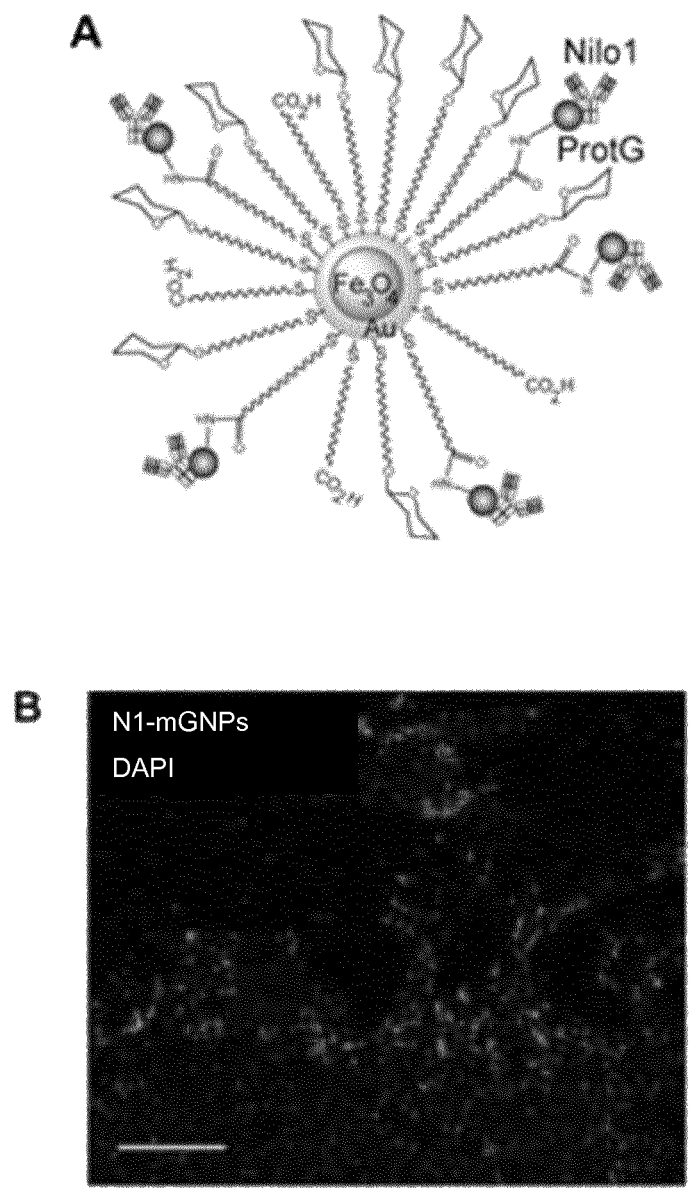
FIG. 2. Nilo1-mGNPs revealed MRI hypointense signals in brain tumor sites. A, Cartoon representing Nilo1-mGNPs. The nanoparticles were made of a magnetic $Fe_3O_4$ core, covered by a gold shell (Au) and subsequently coated with carbohydrates and a carboxyl-ending linker to which Protein G was coupled and Nilo1 mAb bound. B, In vivo identification of SVZ Nilo1$^+$ cells in mice intracranially injected with Nilo1-mGNPs. Brain sections were directly incubated with a secondary biotinylated anti-hamster Ig antibody and revealed with streptavidin A488. DAPI was used to stain nuclei. Scale bar: 25 μm. C, Fluorescence confocal microscopy of Nilo1-mGNPs (top) and Nilo1 mAb (bottom) labeled neurosphere cells grown in Matrigel™. DAPI was used to counter-stain nuclei. Scale bar: 25 μm. D, Flow cytometry analyses of SVZ-derived neurosphere cells stained with Nilo1-mGNPs (light grey) or Nilo1 alone (dark grey) both revealed with a fluorescent secondary antibody. Cells incubated with the secondary antibody in the absence of Nilo1 were used as negative control (black line). E, Schematic representation of the injection sites for the CT-2A astrocytoma cells (left hemisphere, d0) and Nilo1-mGNPs contralaterally in a more rostral position. F, Experimental schedule where Nilo1-mGNPs injection day is indicated with an arrowhead and MRI acquisitions are shown with asterisks, before (empty) or after nanoparticle injection (filled). G, Axial view of T2 MRI image of mouse injected with CT-2A cells (d0) and Nilo1-mGNPs. Dotted line was drawn delimiting the tumor mass. H, Representative T2* MRI study of mice injected with CT-2A cells (d0) and Nilo1-mGNPs (n=3). Axial, coronal and sagittal views just before (−1 h) or 3 h, 22 h, 48 h after nanoparticle injection. Inset in axial panel at 3 h shows the injection site of Nilo1-mGNPs (a more rostral position than the CT-2A injection site). I, Quantification of MRI signal intensity changes from H. The increase in the accumulation of nanoparticles surrounding the tumor is translated as a drop in the mean signal intensity in the region of interest.
Figure 2:
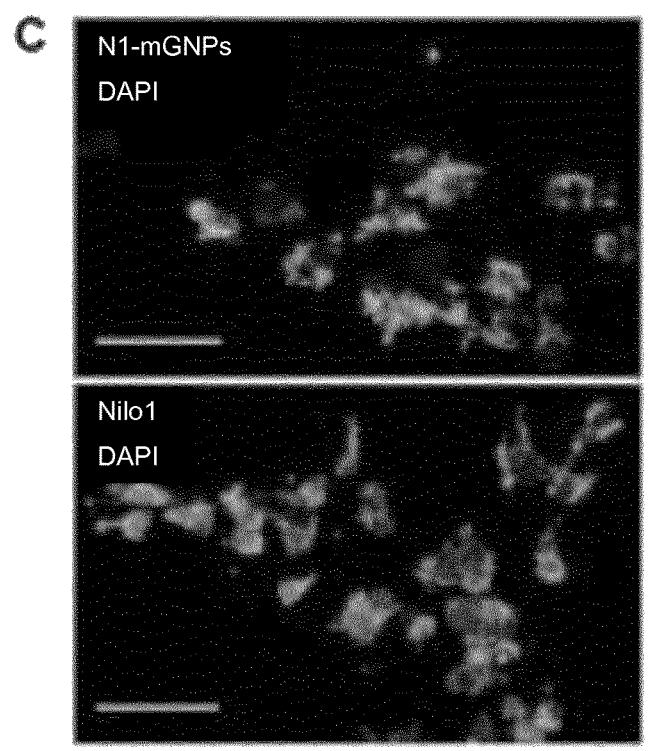
Figure 2:
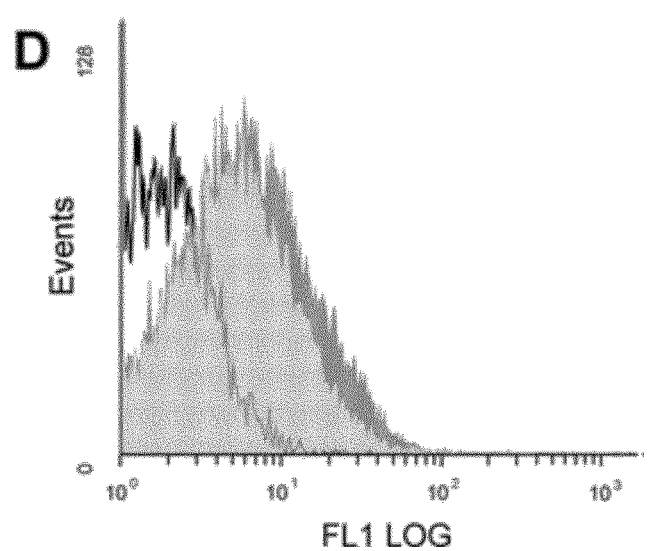
Figure 2:
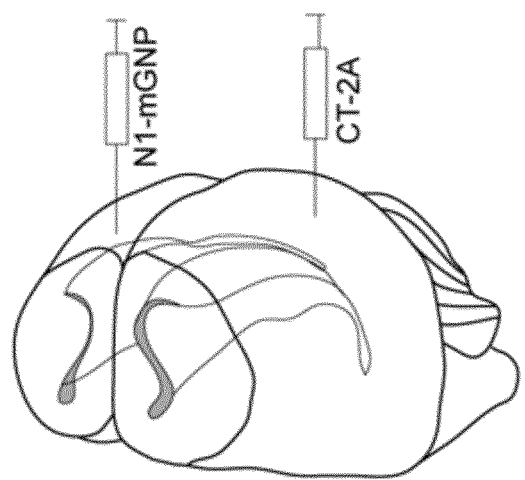
Figure 2:
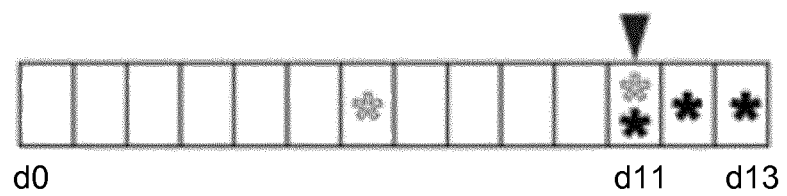
Figure 2:
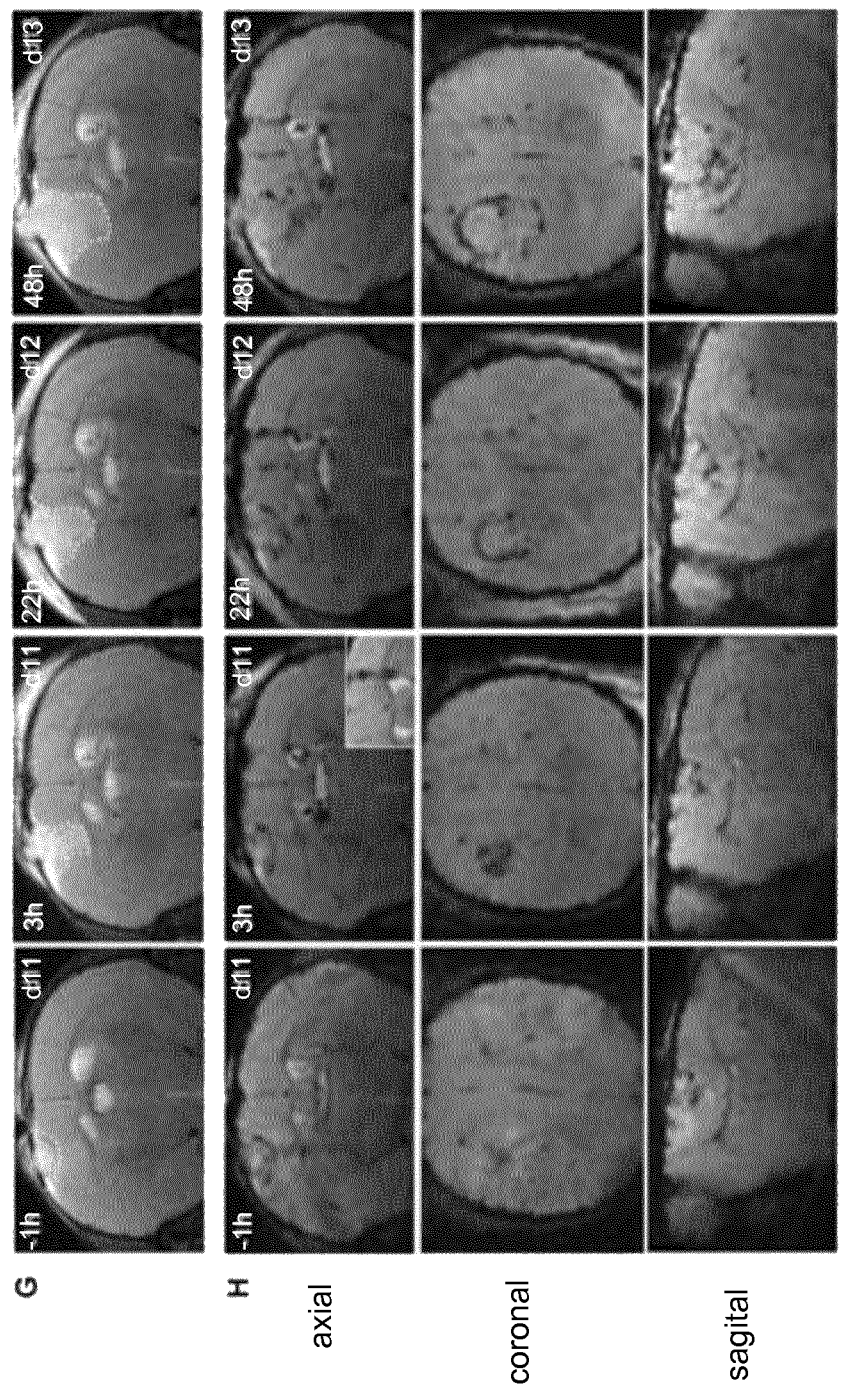
Figure 2:
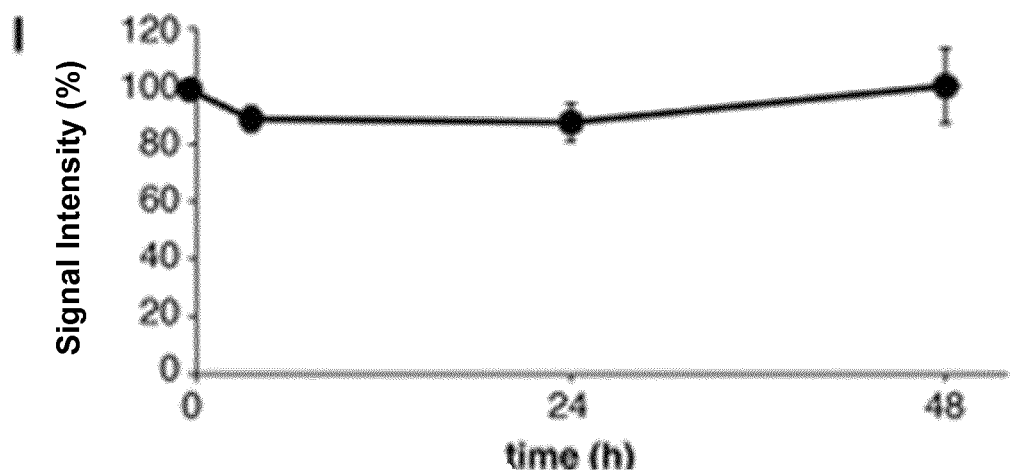

A stereotaxic graft of CT-2A astrocytoma cells ($10^2$-$10^4$ cells) into the left hemisphere (FIG. 2E) generated a highly reproducible glioblastoma at the injection site, which was followed by T2 magnetic resonance imaging (MRI) over time (FIG. 2F), demonstrating that it was grown on day 11 (FIG. 2G). At this time, Nilo1-mGNP complexes were intracranially injected by stereotaxic surgery into the right hemisphere (FIG. 2E, F) of anaesthetized mice, which were subsequently imaged by MRI using T2* sequences (FIG. 2H). T2*-weighted MRI studies obtained one hour before Nilo1-mGNP injection (d11, −1 h) were used as baseline for the experiment. To establish basal hypointensities on the MRI experiments several controls were made, including mice injected with PBS, to evaluate effects due to intracranial surgery; mice injected with CT-2A cells either alone or in combination with an isotopic control antibody (CD3c, developed in hamster) coupled to mGNPs, to evaluate signals due to either tumor growth or unspecific movement of mGNPs. None of this controls showed defined hypointense signals on T2*-weighted MRI studies.

The first T2*MRI study after Nilo1-mGNPs injection (d11, 3 h) allowed to discard that the complexes were directly deposited in the cerebrospinal fluid (inset on FIG. 2H).

At this time, in addition to black spots in the lateral ventricles, which corresponded to Nilo1$^+$ cells in their niches, we detected an increase in the signal hypointensities around the tumor, as compared with the baseline images (FIG. 2H d11, 3 h). These changes could not be explained by neo-vascularization during the four-hour lapse between MRIs. The hypointense T2* signals surrounding the tumor and additional hypointense signals between the niches and the lesion site accumulated over time (FIG. 2H, d12, d13), as quantified in FIG. 2I.

To discard that at longer experimental times, part of the hypointense signals could be due to neo-vascularization associated with tumor growth, we analyzed the Nilo1$^+$ cell migration when the tumor mass was not yet formed (FIG. 3A). For this purpose, CT-2A cells were intracranially injected (d 0) four days after Nilo1-mGNP injection (d-4).

Baseline T2*-weighted MRI images were taken one hour prior to CT-2A injection, failing to detect any hypointense signal at the astrocytoma injection site (FIG. 3B, d0, −1 h). However, as soon as 3.5 hours after injection of the CT-2A cells, an accumulation of hypointense spots at the cell injection site was detected (FIG. 3B, arrowhead d0, 3.5 h) in all analyzed mice. T2-weighted MRI studies (FIG. 3B) enabled the detection of the lesion produced by the stereotaxic injection of the needle to graft the tumor cells (d0, 3.5 h; d2) and the subsequent tumor formation (d7). An increase with time of hypointense signals (T2*-weighted MRI) was detected at this position (FIG. 2B, C) including the needle track (where CT-2A cells could have also been deposited) (d2), accumulating around the tumor when it was formed (d7). During these analyses, tumor induced angiogenesis was undetectable, since in this glioblastoma model increases on days 12 to 14 (FIG. 2H).

To demonstrate that the hypointense signals detected by T2* MRI corresponded to Nilo1$^+$ cells, fixed tissues of the mice used in these MRI experiments were analyzed by immunohistochemistry. Since these tissue sections already contained Nilo1-mGNPs, the presence of Nilo1$^+$ cells was directly revealed with a fluorescently labeled specific secondary antibody.

Figure 3:
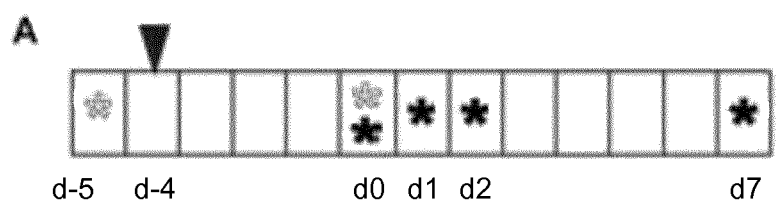
FIG. 3. Migration of B astrocytes towards the tumor site occurs within hours following the insult. A, Experimental schedule where Nilo1-mGNPs injection day is indicated with an arrowhead and MRI acquisitions are shown with asterisks, before (empty) or after tumor cell injection at d0 (filled). B, Representative axial view from the experiment (n=3) showing T2* MRI of a mouse injected with Nilo1-mGNPs (d-4) and CT-2A cells (d0), analyzed just before (−1 h) or 3.5 h, 2 or 7 days after tumor injection (left column). T2 MRI analysis was used to follow tumor growth (right column). Arrowhead indicates hypointense signals accumulated just after tumor cell injection. C, Quantification of MRI signal intensity changes from B. The increase in the accumulation of nanoparticles surrounding the tumor is translated as a drop in the mean signal intensity in the region of interest. D-I, Immunohistochemical analyses of fixed brains from mice analyzed by MRI either twenty-four hours (D-G), or seven days (H, I) after the lesion. Nilo1$^+$ cells were detected by incubation with a secondary biotinilated anti-hamster Ig antibody and revealed with streptavidin A488. Double labeling with DCX (E), EGFR (G) or Sox2 (I). The MRI-hypointense signals detected 3.5 h after tumor cell injection which are maintained and accumulated with time (up to 7 days) corresponded to Nilo1$^+$ cells which had arrived at the lesion site as undifferentiated B astrocytes. LV, lateral ventricle. Scale bars: 50 µm.
Figure 3:
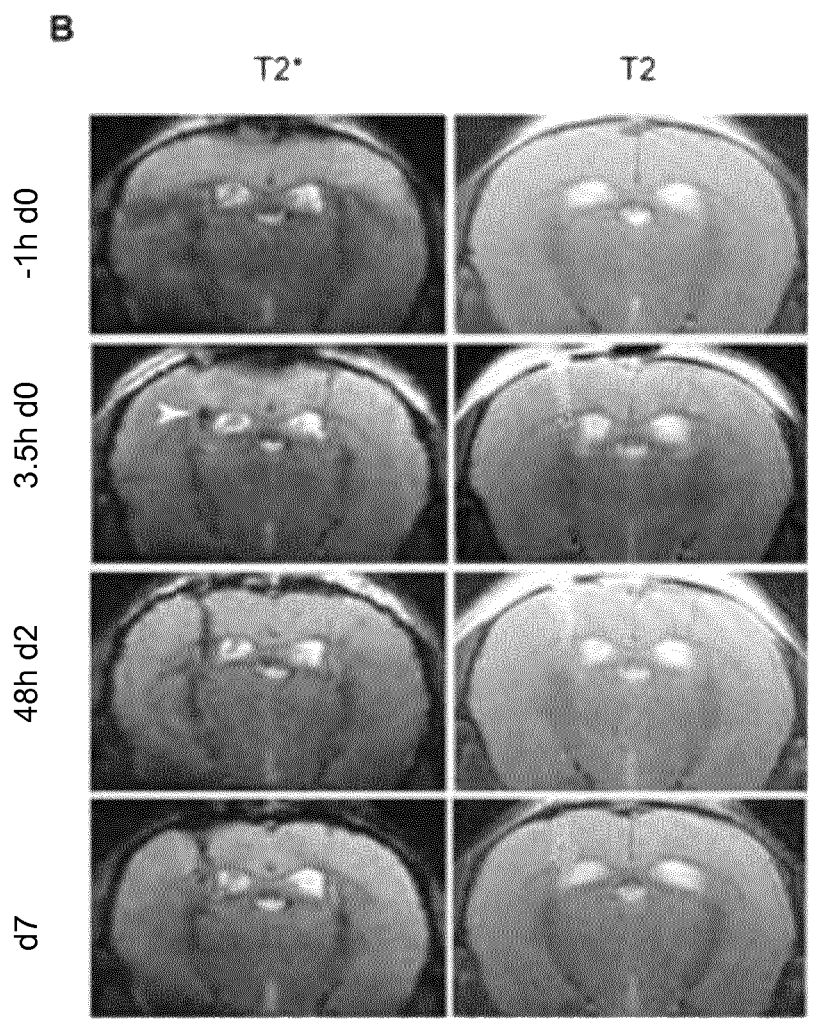
Figure 3:
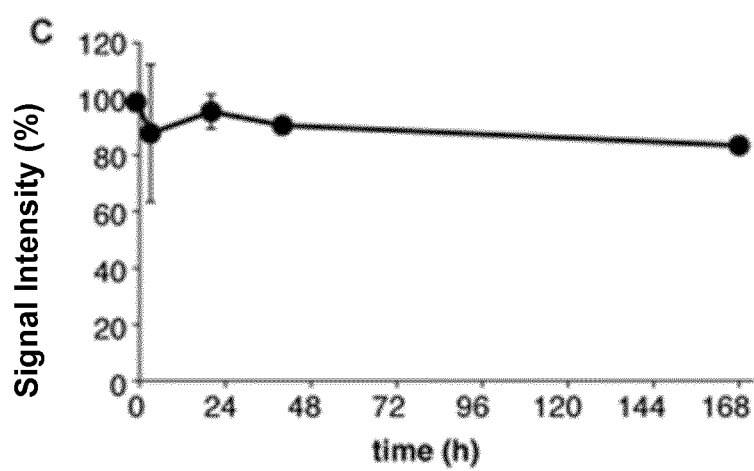
Figure 3:
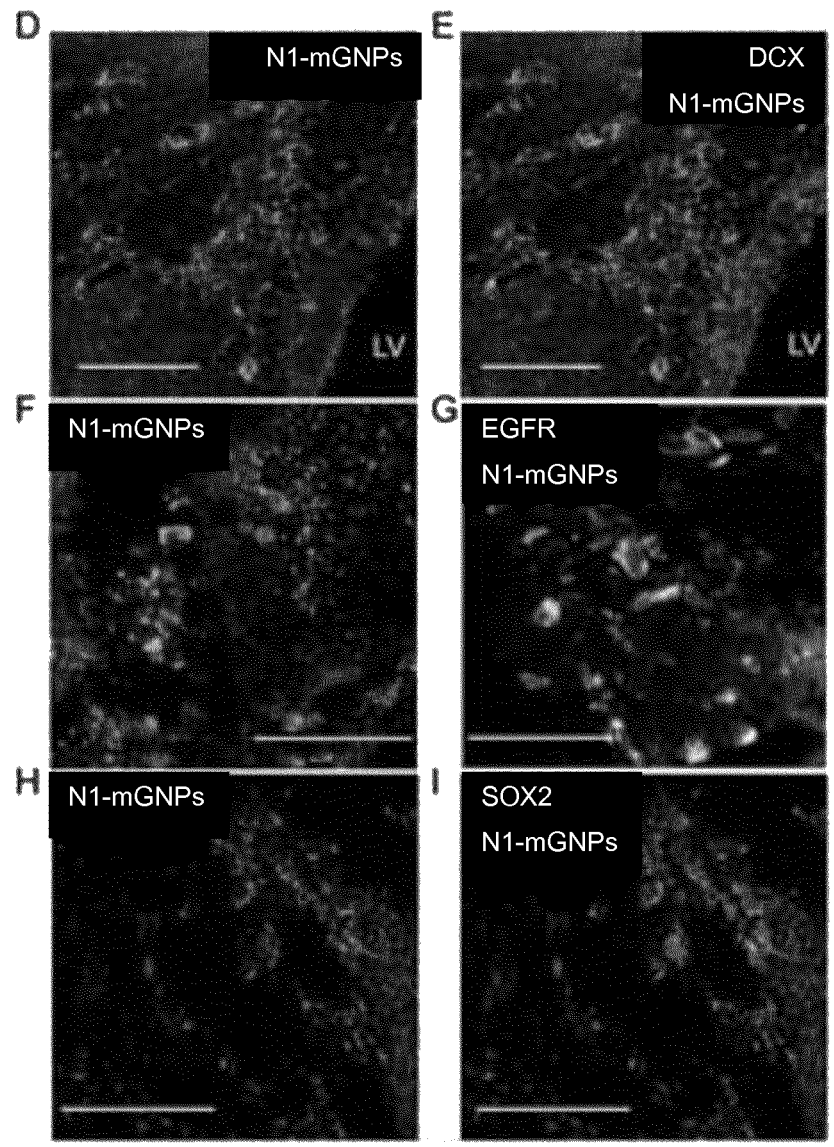

In the experiments where Nilo1-mGNPs were injected before the CT-2A tumor cells, as soon as 24 hours after the damage in the left striatum, we observed a SVZ thickening, concomitant with the presence of neuroblasts (DCX$^+$) and a high number of Nilo1$^+$ cells dispersed outside their usual subependymal location, infiltrating the adjacent striatum (FIG. 3 D, E). This unusual location for Nilo1$^+$ cells could represent cells migrating from the lateral ventricle walls towards the adjacent parenchyma. In addition, in vivo labeled Nilo1$^+$ cells surrounding the lesion site were detected, confirming the MRI data (FIG. 3F). Moreover, Nilo1$^+$ cells were also EGFR$^+$, supporting the notion that these cells arrived undifferentiated at the lesion site (FIG.

3G). Even seven days after the damage, Nilo1$^+$ Sox2$^+$ cells between the niche and the damage site and surrounding the tumor were still detected (FIG. 3 H, I).

Figure 4:
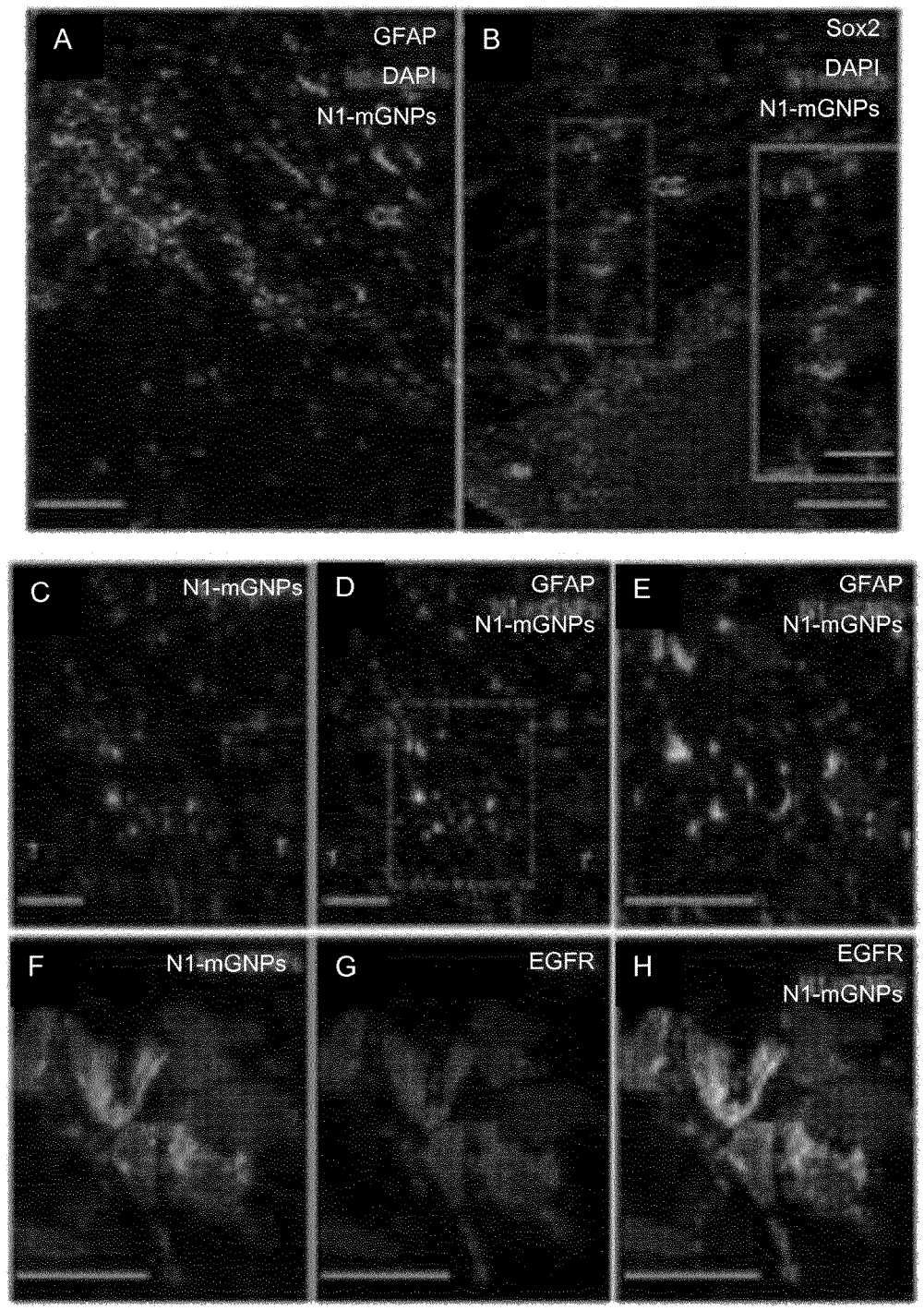
FIG. 4. The MRI hypointense signals surrounding the tumor correspond to B astrocytes. Immunohistochemical analyses of fixed brains from mice analyzed in FIG. 2 two days after the Nilo1-mGNP injection (d13). Since Nilo1 mAb was already present in the Nilo1-mGNPs, Nilo1$^+$ cells were revealed by incubation with a secondary biotinilated anti-hamster Ig antibody and streptavidin-A488. A, B, SVZ ipsilateral to the Nilo1-mGNPs injection site demonstrating the presence of type B astrocytes (Nilo1$^+$ GFAP$^+$ or Nilo1$^+$ Sox2$^+$) exiting the anterior horn (AH) of the lateral ventricle. C-H, Type B astrocytes were also present at the tumor site vicinity since they were Nilo1$^+$ GFAP$^+$ (C-E) or Nilo1$^+$ EGFR$^+$. F-H, Sites with MRI hypointense signals, indicating that Nilo1$^+$ cells migrated to the tumor site as B astrocytes. CC, corpus callosum; T, tumor. Scale bars: A-D, 50 µm; E-H and inset in B, 25 µm.

These data were confirmed by immunohistochemistry analyses on the converse experiment where the CT-2A tumor was formed before the injection of the Nilo1-mGNPs, Nilo1$^+$ cells crossing the corpus callosum from the SVZ towards the lesion site were revealed 3 days after Nilo1-mGNP injection (13 days after tumor injection) (FIG. 4A, B). Conversely, on animals devoid of lesion, Nilo1$^+$ cells were circumscribed to the anterior horn and walls of the lateral ventricles (FIG. 1C), showing the migration specificity of the labeled cells. In addition, Nilo1$^+$ cells expressed additional stem cell markers while migrating (GFAP$^+$ SOX2$^+$) or even at the final destination surrounding the tumor (GFAP$^+$SOX2$^+$EGFR$^+$) (FIG. 4) suggesting that these cells migrated undifferentiated.

2.3. Migration of Nilo1$^+$ Cells is a General Trait for Brain Injury

To ascertain whether the migration of B astrocytes was restricted to the presence of tumor cells or rather to a more generalized response mechanism to brain damage, the presence of type B astrocytes in the neighborhood of three different kinds of brain injuries was analyzed.

Figure 5:
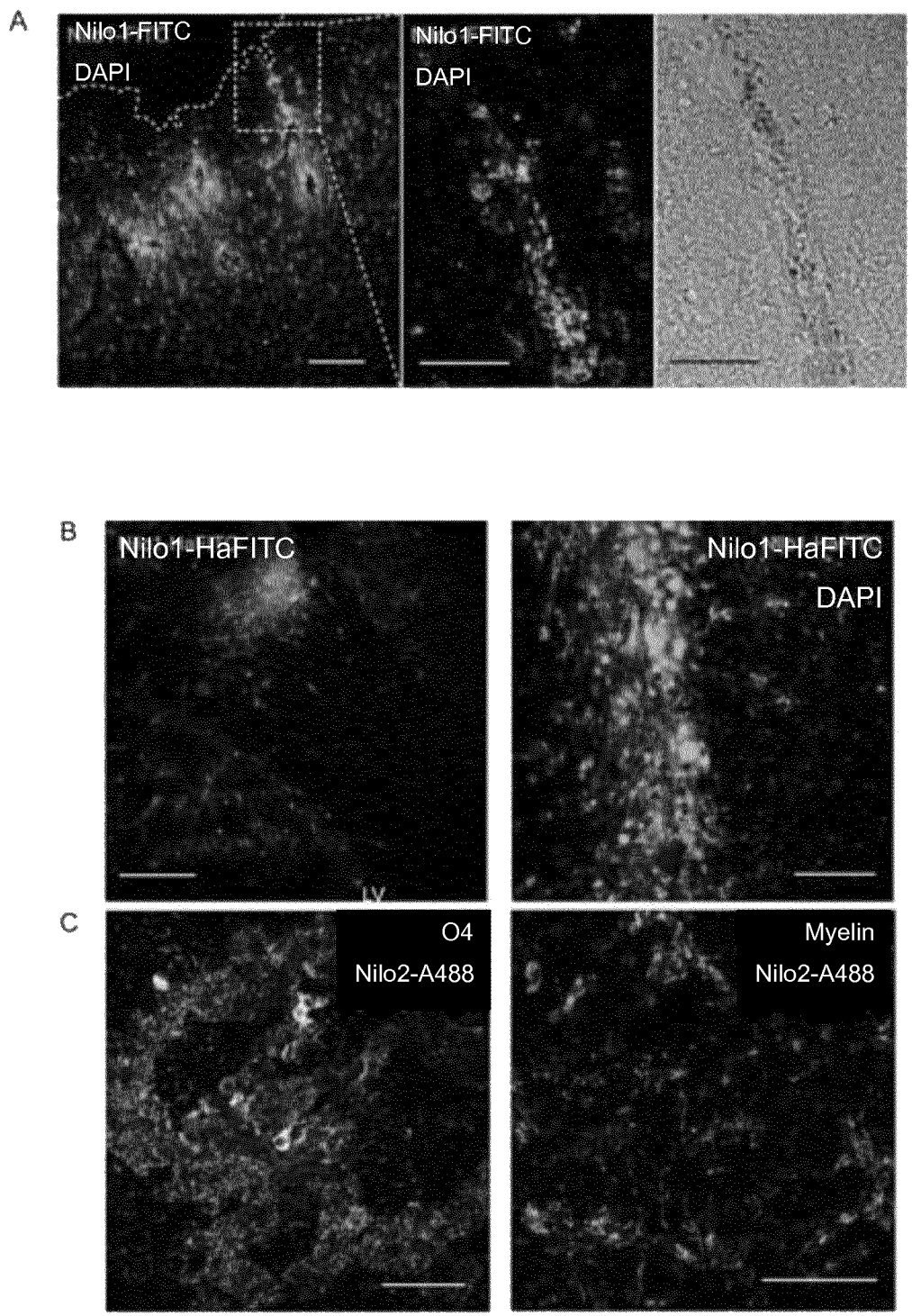
FIG. 5. Migration of B astrocytes occurred following several types of injury. Immunohistochemistry of fixed brains analyzed by confocal microscopy. A, Three days after a cryolesion, Nilo1$^+$ cells were present surrounding the lesion site (dotted line, left panel); magnification showing fluorescent (middle) or bright field (right panel) microscopy where Nilo1$^+$ cells were associated to blood vessels (n=5). B, Seven days following a demyelination, Nilo1$^+$ cells were found between the niche (LV) and the lesion site (left panel) where they accumulated (right panel) (n=3). C, This movement of Nilo1$^+$ cells was followed by the appearance of O4$^+$ and myelin$^+$ cells 25 days after demyelination (n=3). D, Three days after a mechanical damage produced by stereotaxic injection of PBS (n=6), Nilo1$^+$ cells were detected surrounding the lesion site (left panel) revealed by nigrosine (right panel) on a bright field microscopy. E, Three days after a mechanical damage produced by stereotaxic injection of PBS, Nilo2$^+$ neuroblasts were detected filling the lesion site. Scale bars: A and B left panels, 150 µm; A, central and right panels; B right panel, C-E, 50 µm.
Figure 5:
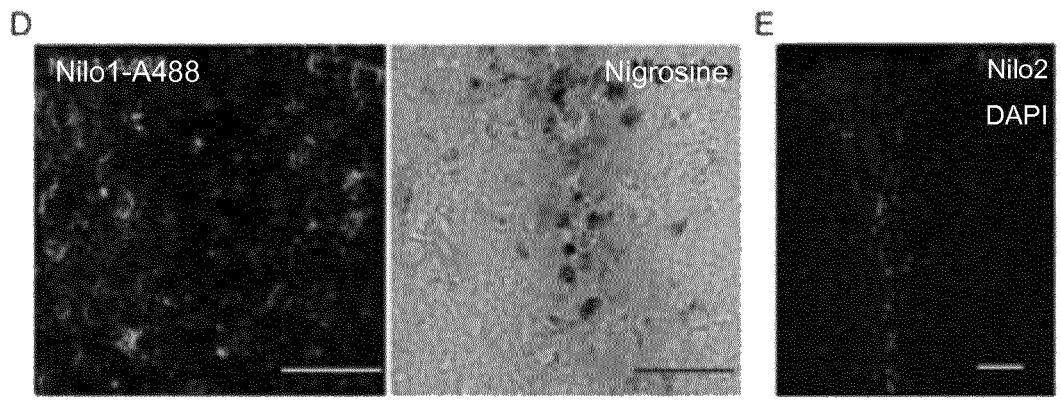

Firstly a cryolesion model was used, which consists on applying dry ice over the left frontal bone for a short time. This model of brain injury generates an initial tissue damage which leads to secondary processes such as cell death, inflammation, vascular edema and blood-brain barrier disruption. In this model Nilo1$^+$ cells were detected on the vicinity of the lesion three days after the injury by immunohistochemistry (FIG. 5A).

In a second lesion model, it was induced a focal demyelinated lesion by lysolecithin (lysophosphatidilcholine, LPC) injection into the left corpus callosum. The initial LPC effect is a localized demyelination during the first week and maintenance of inflammatory signals during the second week. In these mice, seven days after LPC injection, the optimal time for the localized demyelinization, Nilo1$^+$ cell recruitment around the lesion site was detected (FIG. 5B) in sites containing GFAP$^+$ or Sox2$^+$ cells (data not shown). Furthermore, twenty-five days after LPC injection, when remyelination could be confirmed by the presence of O4$^+$ or myelin$^+$ cells, neuroblasts adjacent to remyelinated cells were also detected (FIG. 5C).

The third injury model consisted on a cortical mechanical lesion induced by the puncture with a stereotaxic needle, where the damage site was revealed by injection of nigrosine. Nilo1$^+$ cells migrating to the damage site one to three days after the mechanical injury were detected (FIG. 5D) in a location similar to that where neuroblasts were identified (FIG. 5E).

2.4. Migration of Nilo1$^+$ Cells is Associated with Adult Radial Glia

Figure 6:
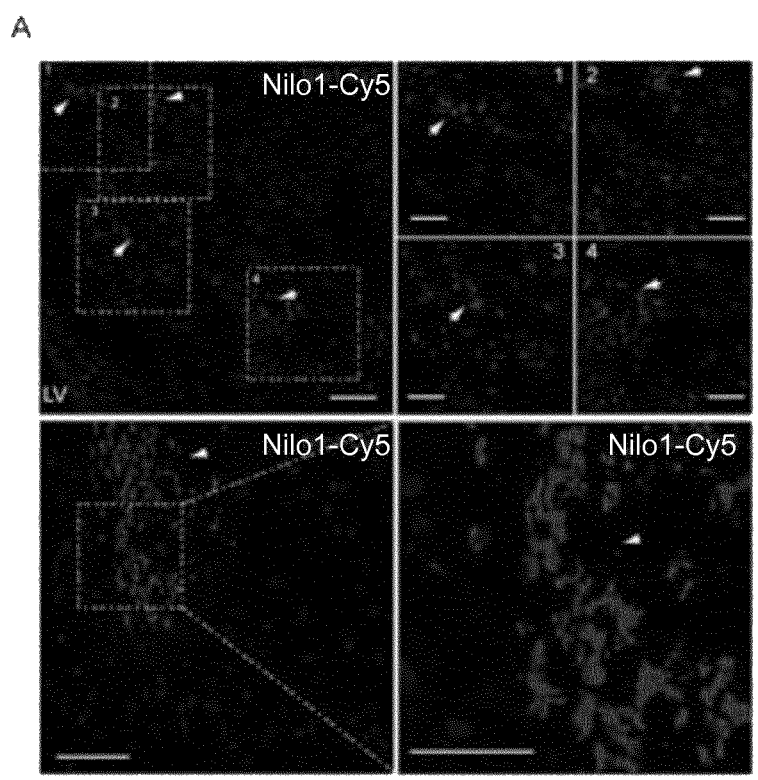
FIG. 6. GFAP$^+$ Nilo1$^+$ processes coalesced and filled the damaged tissue. A, Immunohistochemical analyses of fixed brains from the needle track site on mice intracranially injected with CT-2A cells (top row) (n=3) or PBS (bottom row) (n=3) and analyzed by confocal microscopy 24 hours after the lesion. Staining with Nilo1-Cy5 allows detection, in addition to Nilo1$^+$ cells from SVZ towards the lesion site, of processes that at these early times fill the broken tissue (arrowheads). B, Double immunohistochemistry staining of fixed brains from mice injected with PBS 24 h before, demonstrating that these Nilo1$^+$ processes were compatible with adult radial glia since they were Nilo1$^+$ GFAP$^+$, where associated with PSA-NCAM$^+$ structures and red blood cells Ter-119$^+$, CD24$^+$. These processes did not represent reactive astrocytes since they were vimentin$^-$. LV, lateral ventricle. Scale bars: A, left panels 50 µm, right panels 25 µm; B, 25 µm.
Figure 6:
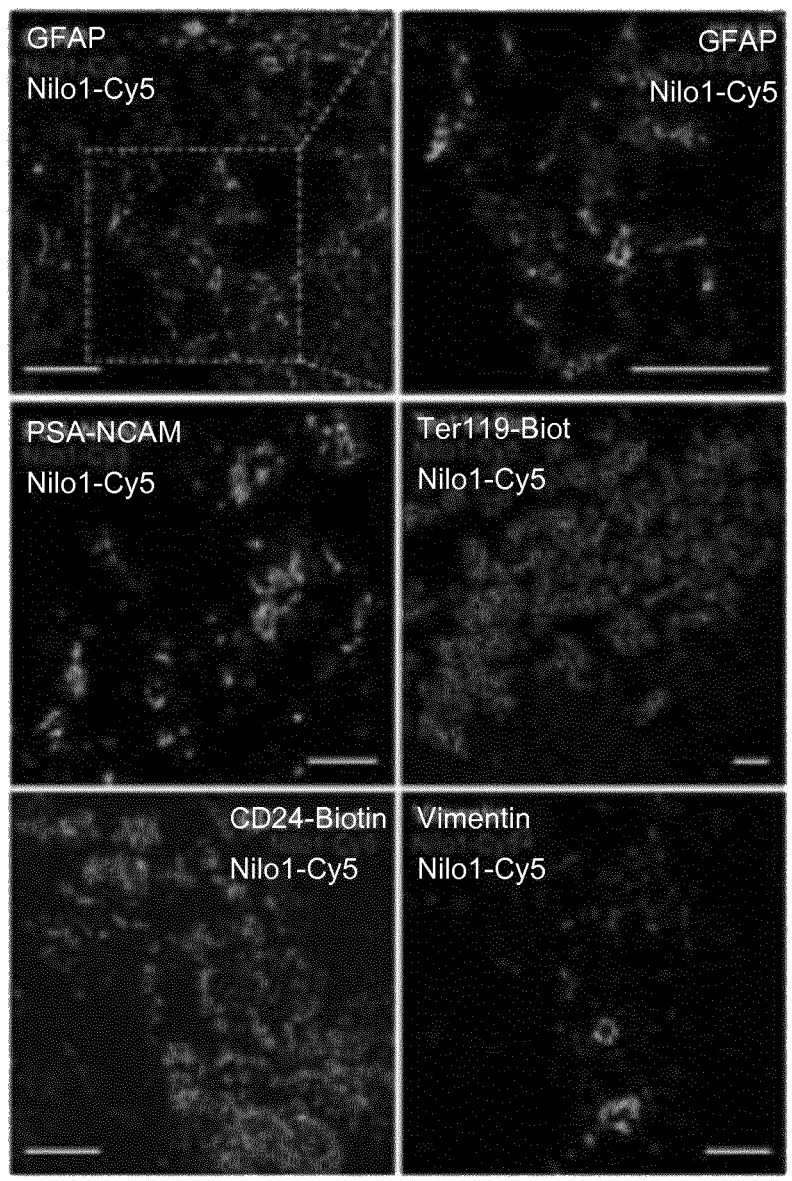

Few hours after injuries produced by needle injection, the wound surrounding the needle track was filled by structures expressing Nilo1 (FIG. 6A). These processes might represent adult radial glia, since they express not only Nilo1 but also the glial marker GFAP, are associated to PSA-NCAM and to the erythrocyte markers Ter119$^+$, CD24$^+$, whereas did not represent reactive astrocytes since they were negative for vimentin and CD11b (FIG. 6B and data not shown).

Figure 7:
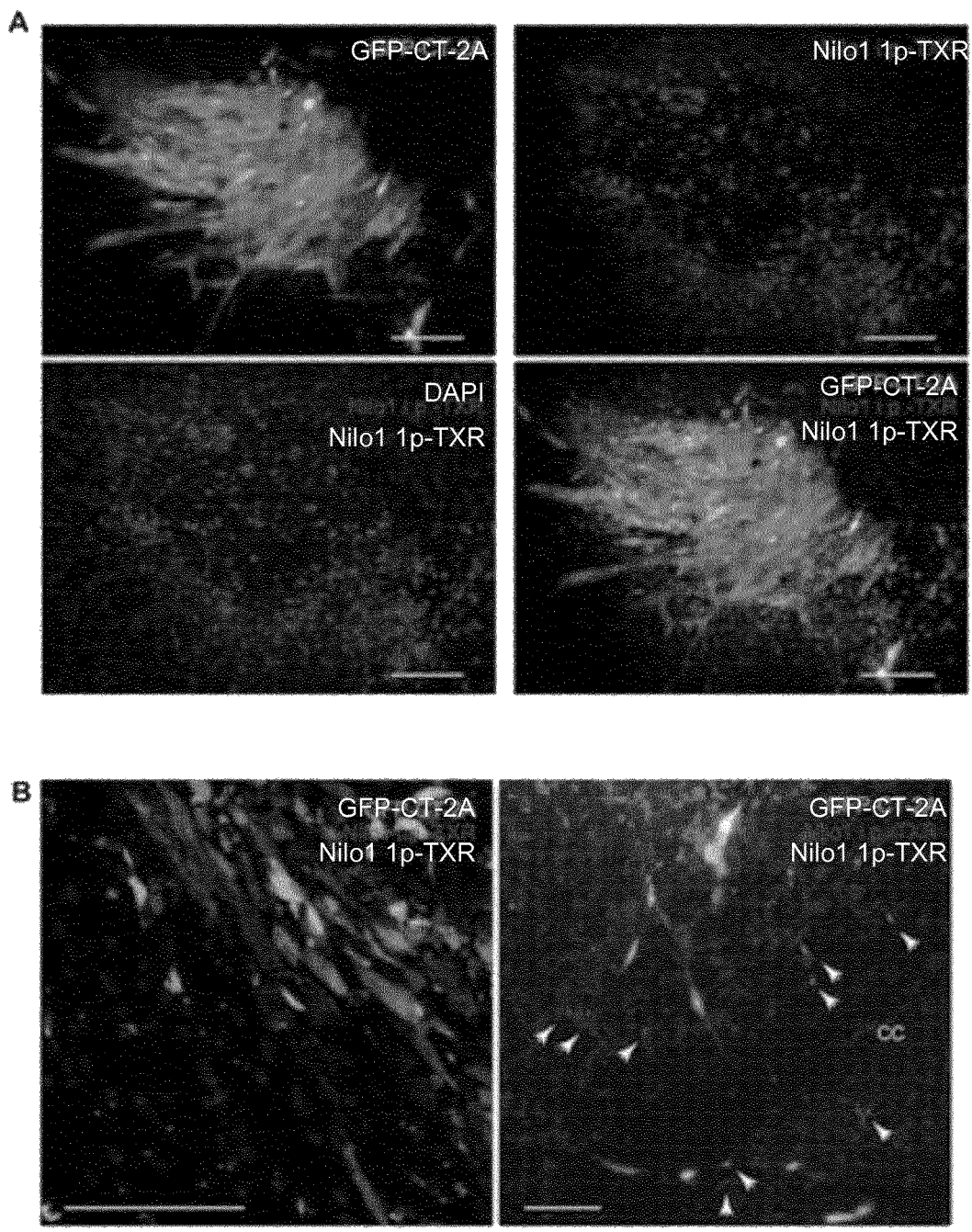
FIG. 7. In vivo identification of B astrocytes surrounding a brain tumor after intraperitoneal injection of the Nilo1 mAb. Immunohistochemical analyses of fixed brain from mice injected with GFP-CT-2A cells (GFP$^+$) in the left striatum, in which Nilo1 was intraperitoneally injected one week after tumor cell injection, and mice (n=4) sacrificed 24 hours later. A, Low and B, high magnification showing that Nilo1$^+$ cells surrounding the tumor were host-derived (left panel). An accumulation of Nilo1$^+$ cells was detected surrounding infiltrated tumor cells (right panel). Nilo1$^+$ cells were revealed with anti-hamster Cy5.5. Scale bars: A, 100 µm; B, 75 µm.

2.5. Intraperitoneally Injected Nilo1 mAb Enables In Vivo Identification of Brain Glioblastomas Since high grade brain tumors induce the blood brain barrier breakdown, one week after intracranially injecting CT-2A-GFP cells, a single dose of Nilo1 mAb (10 µg/g of body weight) was administered intraperitoneally and mice were sacrificed the next day. In the fixed brains, the presence of Nilo1 was revealed by immunohistochemistry with a fluorescently labeled secondary antibody, demonstrating the presence of type B cells surrounding the GFP$^+$ glioblastoma cells (FIG. 7A). The use of GFP tumor cells allowed the identification of host cells (Nilo1$^+$ GFP$^-$, arrowheads in FIG. 7B) in areas where isolated tumor cells infiltrated the parenchyma. This experiment corroborated the notion that type B astrocytes migrate towards the tumor site and opens up the possibility of using intraperitoneally injected antibodies to follow brain damage in situations where the blood brain barrier is disrupted.

3. Conclusions

Although there are evidences that immature neurons present in brain lesion sites, such as peri-infarcted tissue, come from GFAP$^+$ SVZ-derived neural stem cells, a direct mobilization of type B astrocytes towards a lesion site had not yet been reported.

To study the migration of early neural progenitors towards a brain injury, Nilo1 mAb was used in the present invention. Here it has been demonstrated that Nilo1 identified type B astrocytes (or adult neural stem cells) since i) it recognized GFAP$^+$, Sox2$^+$ and EGFR$^+$ cells, being negative for the neuroblast marker DCX; ii) Nilo1 did not stain ependymal CD24$^+$ cells, having instead subependymal localization on the SVZ; iii) transient amplifying cells (or type C cells, which are Pax6$^{high}$BrdU$^+$ on tissue sections from in vivo labeled animals with a short BrdU pulse) and Nilo1$^+$ cells represented two distinct populations; iv) Nilo1$^+$ cells were GFAP$^+$, excluding the possibility that this mAb identified intermediate progenitors in the differentiation process, like NG2-precursors which are GFAP$^-$; v) double staining of E10 embryo brains with Nilo1 and either vimentin or nestin suggested that Nilo1 recognizes embryonic radial glia.

Nilo1 mAb, coupled to functionalized-magnetic nanoparticles in combination with magnetic resonance imaging allowed to identify the Nilo1$^+$ cells at their niche in the SVZ and, in animals carrying a lesion, at intermediate positions between the niche and the lesion site, where they accumulated over time. The migratory response was very fast since MRI hypointense signals at the lesion site were detected by MRI 3 h after injection of the Nilo1-mGNP complexes in animals bearing tumors, or 3.5 h after injection of the CT-2A cells on animals that had previously been injected with Nilo1-mGNP complexes. The presence of Nilo1$^+$ cells at the lesion site was corroborated by immunohistochemistry analysis on fixed brain sections from these mice, incubating with a fluorescent secondary antibody, since the Nilo1$^+$ cells were already labeled in vivo with the Nilo1-mGNPs. Immunohistochemistry confirmed not only that the hypointense signals corresponded to Nilo1$^+$ cells surrounding the tumor, but also that these cells retained their type B astrocyte phenotype (GFAP$^+$, EGFR$^+$, Sox2$^+$) following their migration.

The migration of adult neural stem cells (type B astrocytes) towards a tumor site, rather than a tumor-specific response, turned out to be a more generalized response to brain insults since Nilo1$^+$ cells at the sites where other types of lesions were produced were also detected (i.e. cryolesion, demyelination, mechanical injury). These lesions were chosen because they are very different from each other and from the tumor implantation model described above. In all of them, Nilo1$^+$ cells were detected surrounding the lesions.

In addition to Nilo1+ cells migrating to the lesion sites, both in a mechanical lesion model and after any stereotactic injection, it was detected, one day after the lesion, coalescing structures filling the wound-lesion that expressed high levels of Nilo1 antigen. These Nilo1+ processes were GFAP+, vimentin− and CD11b−, forming structures associated to PSA-NCAM. On the one hand, the observation that these structures did not express vimentin or CD11b allowed to exclude that they represented proximal reactive astrocytes. On the other hand, their GFAP+ staining was compatible with the presence of adult radial glia fibers or glial tubes. Radial glia cells have been defined as neuronal precursors and it has been suggested that they could represent a specific subpopulation of astrocytes in adult mammals. Furthermore, the presence of radial glia in adult hippocampus where neurogenesis occurs throughout life, or in non-mammalian vertebrates where neurogenesis persists in a rather wide-spread fashion in the adult brain, raise the possibility that the neurogenic potential of radial glia may extend into adulthood in some brain regions or even as an acute response to brain lesions, were neurogenesis is necessary and commonly associated to brain tissue repairing processes.

The migration of neural stem cells reported here is in fully accordance with data showing that stimulation with exogenous growth factors increase cell proliferation at the SVZ and promote the migration of SVZ-derived cells into the adjacent parenchyma or even at the vicinity of a brain lesion site.

Finally, the data presented here represents a proof that MRI using Nilo1-GMPs can be used in humans for detection of a brain primary tumor or a recidive very early on, before contrast substances such as gadolinium would give a detectable signal. In particular, since it has been shown herein that Nilo1 mAb is able to also identify the corresponding antigens present in cells derived from human glioblastomas.

The invention claimed is:

1. A method for the treatment of brain tumors or brain lesions comprising administering to a subject in need thereof an effective amount of a monoclonal antibody, NILO1, produced by the hybridoma deposited under the DSM accession number No. ACC2887, wherein the antibody is coupled to an active principle and wherein the active principle is for the treatment of brain tumors and brain lesions.

2. The method according to claim 1, wherein the antibody is humanized.

3. The method according to claim 1 wherein the brain lesion is produced by a neurodegenerative process, demyelination, mechanical injury or stroke, and the brain tumor is glioblastoma.

4. The method according to claim 1 wherein the active principle is a drug.

5. A method for the diagnosis of a brain tumor or brain lesion, which comprises:
  a. intraperitoneally injecting a monoclonal antibody, NILO1, produced by the hybridoma deposited under the DSM accession number No. ACC2887, in the brain of a subject,
  b. detecting the presence of cells marked with the antibody, and
  c. associating the presence of said marked cells to a brain tumor or brain lesion.

6. The method according to claim 5, wherein the antibody is coupled to a support or a particle.

7. The method according to claim 6 wherein the particle is a magnetic glyconanoparticle.

8. The method according to claim 5 wherein the brain lesion is produced by a neurodegenerative process, demyelination, mechanical injury or stroke, and the brain tumor is glioblastoma.

* * * * *